United States Patent
Sharif et al.

(10) Patent No.: US 10,706,592 B2
(45) Date of Patent: Jul. 7, 2020

(54) SYSTEMS AND METHODS FOR MYOCARDIAL PERFUSION MRI WITHOUT THE NEED FOR ECG GATING AND ADDITIONAL SYSTEMS AND METHODS FOR IMPROVED CARDIAC IMAGING

(71) Applicant: Cedars-Sinai Medical Center, Los Angeles, CA (US)

(72) Inventors: Behzad Sharif, Los Angeles, CA (US); Debiao Li, South Pasadena, CA (US); Daniel S. Berman, Los Angeles, CA (US); C. Noel Bairey Merz, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1121 days.

(21) Appl. No.: 14/590,935

(22) Filed: Jan. 6, 2015

(65) Prior Publication Data
US 2015/0192653 A1    Jul. 9, 2015

Related U.S. Application Data

(60) Provisional application No. 61/924,155, filed on Jan. 6, 2014.

(51) Int. Cl.
*G06T 11/00* (2006.01)
*A61B 5/055* (2006.01)
(Continued)

(52) U.S. Cl.
CPC .......... *G06T 11/003* (2013.01); *A61B 5/0037* (2013.01); *A61B 5/0044* (2013.01);
(Continued)

(58) Field of Classification Search
CPC .......... A61B 2576/023; A61B 5/0037; A61B 5/0044; A61B 5/055; A61B 5/7275;
(Continued)

(56) References Cited

U.S. PATENT DOCUMENTS

| | | | |
|---|---|---|---|
| 2007/0135705 A1* | 6/2007 | Lorenz | A61B 5/055 600/410 |
| 2011/0181285 A1* | 7/2011 | Greiser | A61B 5/055 324/309 |

(Continued)

OTHER PUBLICATIONS

Salerno et al. "Improved first-pass spiral myocardial perfusion imaging with variable density trajectories." Magn. Reson. Med. 70:1369-1379 (2013).*

(Continued)

*Primary Examiner* — Amelie R Davis
(74) *Attorney, Agent, or Firm* — Nixon Peabody LLP

(57) ABSTRACT

In some embodiments, the present application discloses systems and methods for cardiac MRI that allow for continuous un-interrupted acquisition without any ECG/cardiac gating or synchronization that achieves the required image contrast for imaging perfusion defects. The invention also teaches an accelerated image reconstruction technique that is tailored to the data acquisition scheme and minimizes or eliminates dark-rim image artifacts. The invention further enables concurrent imaging of perfusion and myocardial wall motion (cardiac function), which can eliminate the need for separate assessment of cardiac function (hence shortening exam time), and/or provide complementary diagnostic information in CAD patients.

12 Claims, 20 Drawing Sheets

(51) Int. Cl.

| | |
|---|---|
| *A61B 5/00* | (2006.01) |
| *G01R 33/48* | (2006.01) |
| *G01R 33/563* | (2006.01) |
| *G16H 30/40* | (2018.01) |
| *G16H 40/60* | (2018.01) |
| *G16H 50/50* | (2018.01) |
| *G01R 33/56* | (2006.01) |

(52) U.S. Cl.
CPC ............ *A61B 5/055* (2013.01); *A61B 5/7275* (2013.01); *G01R 33/4824* (2013.01); *G01R 33/56366* (2013.01); *G16H 30/40* (2018.01); *G16H 40/60* (2018.01); *G16H 50/50* (2018.01); *A61B 2576/023* (2013.01); *G01R 33/5601* (2013.01)

(58) Field of Classification Search
CPC ............ G01R 33/4824; G01R 33/5601; G01R 33/56366; G06T 11/003; G16H 30/40; G16H 40/60; G16H 50/50
See application file for complete search history.

(56) References Cited

U.S. PATENT DOCUMENTS

| | | | | |
|---|---|---|---|---|
| 2011/0234222 | A1* | 9/2011 | Frahm ................ | G01R 33/4824 324/309 |
| 2014/0062477 | A1* | 3/2014 | Carroll ............... | G01R 33/4826 324/309 |
| 2014/0296700 | A1* | 10/2014 | Gulani ............... | G01R 33/3614 600/414 |
| 2015/0077112 | A1* | 3/2015 | Otazo ................... | A61B 5/055 324/318 |
| 2016/0169999 | A1* | 6/2016 | Herza ................... | A61B 5/055 600/411 |

OTHER PUBLICATIONS

Guttman et al. "Imaging of Myocardial Infarction for Diagnosis and Intervention Using Real-Time Interactive MRI Without ECG-Gating or Breath-Holding." Author manuscript; available in PMC Aug. 6, 2007 Published in final edited form as Magn. Reson. Med. Aug. 2004; 52(2): 354-361. (Year: 2004).*
Block et al. "Model-Based Iterative Reconstruction for Radial Fast Spin-Echo MRI." IEEE Transactions on Medical Imaging, vol. 28, Issue: 11, Nov. 2009. pp. 1759-1769. (Year: 2009).*
Steady-state free precession MRI.Radiopaedia.org. https://radiopaedia.org/articles/steady-state-free-precession-mri-2?lang=us (Year: 2019).*
Adluru, G. et al., Acquisition and reconstruction of undersampled radial data for myocardial perfusion MRI, J. Magn Reson Imaging, 2009, 29(2):466-473.
Block, K.T. et al., Radial Single Shot STEAM MRI, Magn Reson Med, 2008, 59:686-691.
DiBella, E.V.R. et al., On the dark rim artifact in dynamic contrast-enhanced MRI myocardial perfusion studies, Magn Reson Med, 2005, 54:1295-1299.
Fessler, J.A., On NUFFT-based gridding for non-Cartesian MRI, Journal of Magnetic Resonance, 2007, 188(2):191-195.
Griswold, M.A. et al., Generalized autocalibrating partially parallel acquisitions (GRAPPA), Magn Reson Med, 2002, 47:1202-1210.
Naylor, D.A. et al., Apodizing functions for Fourier transform spectroscopy, J Opt Soc Am A, 2007, 24(11):3644-3648.
Peters, D.C. et al., Centering the projection reconstruction trajectory: Reducing gradient delay errors, Magn Reson Med, 2003, 50(1):1-6.
Peters, D.C. et al., Inversion recovery radial MRI with interleaved projection sets, Magn Reson Med, 2006, 55:1150-1156.
Peters, D.C. et al., Myocardial wall tagging with undersampled projection reconstruction, Magn Reson Med, 2001, 45(4):562-567.
Plein, S. et al., Dynamic contrast-enhanced myocardial perfusion MRI accelerated with k-t SENSE, Magn Reson Med, 2007, 58:777-785.
Pruessmann, K.P. et al., Advances in sensitivity encoding with arbitrary k-space trajectories, Magn Reson Med, 2001, 46:638-651.
Salerno, M. et al., Myocardial perfusion imaging with variable density spiral trajectories, in proceedings of the 18th Annual Meeting of ISMRM, 2010, p. 3624.
Scheffler, K. et al., Reduced circular field-of-view imaging, Magn Reson Med, 1998, 40:474-480.
Shankaranarayanan, A. et al., Segmented k Space and real time cardiac cine MR imaging with radial trajectories, Radiology, 2001, 221:827-836.
Walsh, D. O. et al., Adaptive reconstruction of phased array MR imagery, Magn Reson Med, 2000, 43:682-690.
Winkelmann, S. et al., An optimal radial profile order based on the Golden Ratio for time-resolved MRI, IEEE Trans. Med. Imaging, 2007, 26(1):68-76.
Giri et al., Steady-State First-Pass Perfusion (SSFPP): A New Approach to 3D First-Pass Myocardial Perfusion Imaging, Magn Reson Med., (2014) 71:133-144.
Kellman et al., Imaging Sequences for First Pass Perfusion—A Review, J Cardiovasc Magn Res., (2007) 9, 525-537.
Maredia et al., Effect of Improving Spatial or Temporal Resolution on image Quality and Quantitative Perfusion Assessment with k-t SENSE Acceleration in First-Pass CMR Myocardial Perfusion Imaging, Magn Reson Med., (2010) 64:1616-1624.

* cited by examiner

SYSTEMS AND METHODS FOR MYOCARDIAL PERFUSION MRI WITHOUT THE NEED FOR ECG GATING AND ADDITIONAL SYSTEMS AND METHODS FOR IMPROVED CARDIAC IMAGING

CROSS REFERENCE TO RELATED APPLICATION

This application claims priority under 35 U.S.C. § 119(e) from U.S. Provisional Application No. 61/924,155 filed Jan. 6, 2014, which is incorporated herein by reference in its entirety.

STATEMENT REGARDING FEDERALLY SPONSORED RESEARCH OR DEVELOPMENT

This invention was made with government support under Grant Nos. EB002623, HL090957, RR000425, and HL124323 awarded by the National Institutes of Health. The government has certain rights in the invention.

FIELD OF THE INVENTION

The present invention generally relates to imaging methods and systems.

BACKGROUND

The following description includes information that may be useful in understanding the present invention. It is not an admission that any of the information provided herein is prior art or relevant to the presently claimed invention.

A decrease in stress myocardial perfusion represents an early marker reflecting the functional effects associated with abnormalities in the coronary arteries. To date, myocardial perfusion imaging (MPI) is most commonly assessed using nuclear imaging modalities. Stress cardiac magnetic resonance (CMR) is not yet widely used—particularly in the United States; however, multiple multicenter trials have demonstrated higher accuracy in detection of obstructive coronary artery disease (CAD) with CMR than with SPECT MPI. With recent hardware and software improvements, vasodilator stress CMR first-pass perfusion imaging is emerging as an attractive alternative, providing comprehensive cardiac assessment with a radiation-free approach.

Despite significant technical advances during the past decade, persistent problems have limited the widespread use of perfusion CMR. One problem is that CMR is a complex method far more dependent on the expertise of the technologist than nuclear myocardial perfusion imaging, and in general is considered to be a complicated modality for diagnosis of CAD. A major source of complexity has been the need for near-perfect ECG gating.

A second problem is that stress MRI studies are commonly associated with an artifact that makes image interpretation difficult even for experts. This image artifact is referred to as the subendocardial dark-rim artifact. In the perfusion image series, dark-rim artifacts are most pronounced when the contrast bolus first washes into the left ventricular cavity—particularly during the stress portion of the examination. The artifact lasts for a few heartbeats, and mimics true perfusion defects. Consequently, dark-rim artifacts remain a major drawback for accuracy and wide-spread adoption of perfusion MRI since they impede diagnosis of hypoperfusion in the subendocardium, which is the myocardial layer characteristically seen to have abnormality in ischemic heart disease.

Stress perfusion imaging with CMR offers the promise of providing a comprehensive cardiac examination without radiation. Its high resolution allows for distinguishing subendocardial from subepicardial hypoperfusion, something that cannot be resolved by nuclear methods. This quality of perfusion CMR could overcome the problem associated with "balanced reduction of flow" that is known to be a mechanism by which nuclear MPI can miss the most high risk forms of the disease.

In view of all of the aforementioned considerations, there is clearly a need in the art for an improved CMR perfusion technique that eliminates the need for ECG gating altogether and produces images free of the dark-rim artifact.

SUMMARY OF THE INVENTION

In various embodiments, the invention teaches a method for performing first-pass myocardial perfusion magnetic resonance imaging (MRI). In some embodiments, the method includes: (1) using an MRI machine to apply a pulse sequence with radial k-space sampling to a volume of interest (VOI) including a region of a subject's heart; (2) introducing a contrast agent into the subject's vascular system prior to or during imaging; and (3) using a model-based/iterative image reconstruction technique to generate one or more images of one or more slices or VOIs within the heart region. In some embodiments, no electrocardiogram (ECG) signal acquisition is required during the MRI. In certain embodiments, an apodization scheme is employed in the image reconstruction technique to reduce or eliminate a dark-rim artifact. In some embodiments, one or more of the images depict the heart or a portion thereof within 30 to 60 heartbeats after injection of the contrast agent. In certain embodiments, multiple image frames are generated per each heartbeat at a rate of at least 8 frames per second to depict the heart motion. In some of these embodiments, an apodization scheme is employed in the image reconstruction technique to reduce or eliminate a dark-rim artifact. In certain embodiments, the MRI machine is a 3.0T scanner. In some embodiments, the subject has an arrhythmia.

In various embodiments, the invention teaches a method for performing cardiac magnetic resonance imaging (MRI). In certain embodiments, the method includes (1) using an MRI machine to apply an ungated gradient recalled echo (GRE) pulse sequence with continuous radial acquisition to a volume of interest (VOI) including a region of a subject's heart; and (2) using an iterative parallel imaging or sensitivity encoding image reconstruction technique to generate one or more images of one or more anatomical structures within the VOI in the subject. In some embodiments, the method further includes introducing a contrast agent into the subject's vascular system prior to or during imaging. In certain embodiments, an apodization scheme is employed in the image reconstruction technique to reduce or eliminate a dark-rim artifact. In some embodiments, the MRI machine is a 3.0T scanner. In certain embodiments, the subject has an arrhythmia. In some embodiments, multiple image frames are generated per each heartbeat at a rate of at least 8 frames per second to depict the heart motion. In certain embodiments, the method further includes diagnosing the subject with the presence or absence of a condition associated with a perfusion defect or a wall motion abnormality, based upon one or more of the images generated.

In various embodiments, the invention teaches a method for performing cardiac magnetic resonance imaging (MRI). In some embodiments, the method includes (1) using an MRI machine to apply an ungated gradient recalled echo (GRE) pulse sequence with continuous radial sampling to a volume of interest (VOI) in a subject, wherein the VOI includes a region of the subject's heart; (2) introducing a contrast agent into the subject's vascular system prior to or during imaging; and (3) using an iterative image reconstruction scheme to generate one or more images of one or more anatomical structures within the VOI. In certain embodiments, an apodization scheme is employed in the image reconstruction technique to reduce or eliminate a dark-rim artifact. In some embodiments, multiple image frames are generated per each heartbeat at a rate of at least 8 frames per second to depict the heart motion. In some embodiments, the method further includes diagnosing the subject with the presence or absence of a condition associated with a perfusion defect, based upon one or more of the images generated. In certain embodiments, the MRI machine is a 3.0T scanner. In certain embodiments, the subject has an arrhythmia.

In various embodiments, the invention teaches a magnetic resonance imaging system. In some embodiments, the system includes (1) a magnet operable to provide a magnetic field; (2) a transmitter operable to transmit to a region within the magnetic field; (3) a receiver operable to receive a magnetic resonance signal from the region; and (4) a processor operable to control the transmitter and the receiver; wherein the processor is configured to direct the transmitter and receiver to execute a sequence, including (a) applying any of the pulse sequences described herein to a volume of interest (VOI) in a subject, wherein the VOI includes a region of the subject's heart; (b) acquiring magnetic resonance data from the (VOI) in the subject; and (c) generating one or more images using any of the image generating methods described herein, wherein the processor is configured to generate an image based on the magnetic resonance data.

In various embodiments, the invention teaches a non-transitory machine-readable medium having machine executable instructions for causing one or more processors of a magnetic resonance imaging (MRI) machine to execute a method, including: (1) applying any of the pulse sequences described herein to a volume of interest (VOI) in a subject, wherein the VOI comprises a region of the subject's heart; (2) acquiring magnetic resonance data from the volume of interest (VOI) in the subject; and (3) generating one or more images based on the magnetic resonance data using any suitable imaging generating method described herein.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
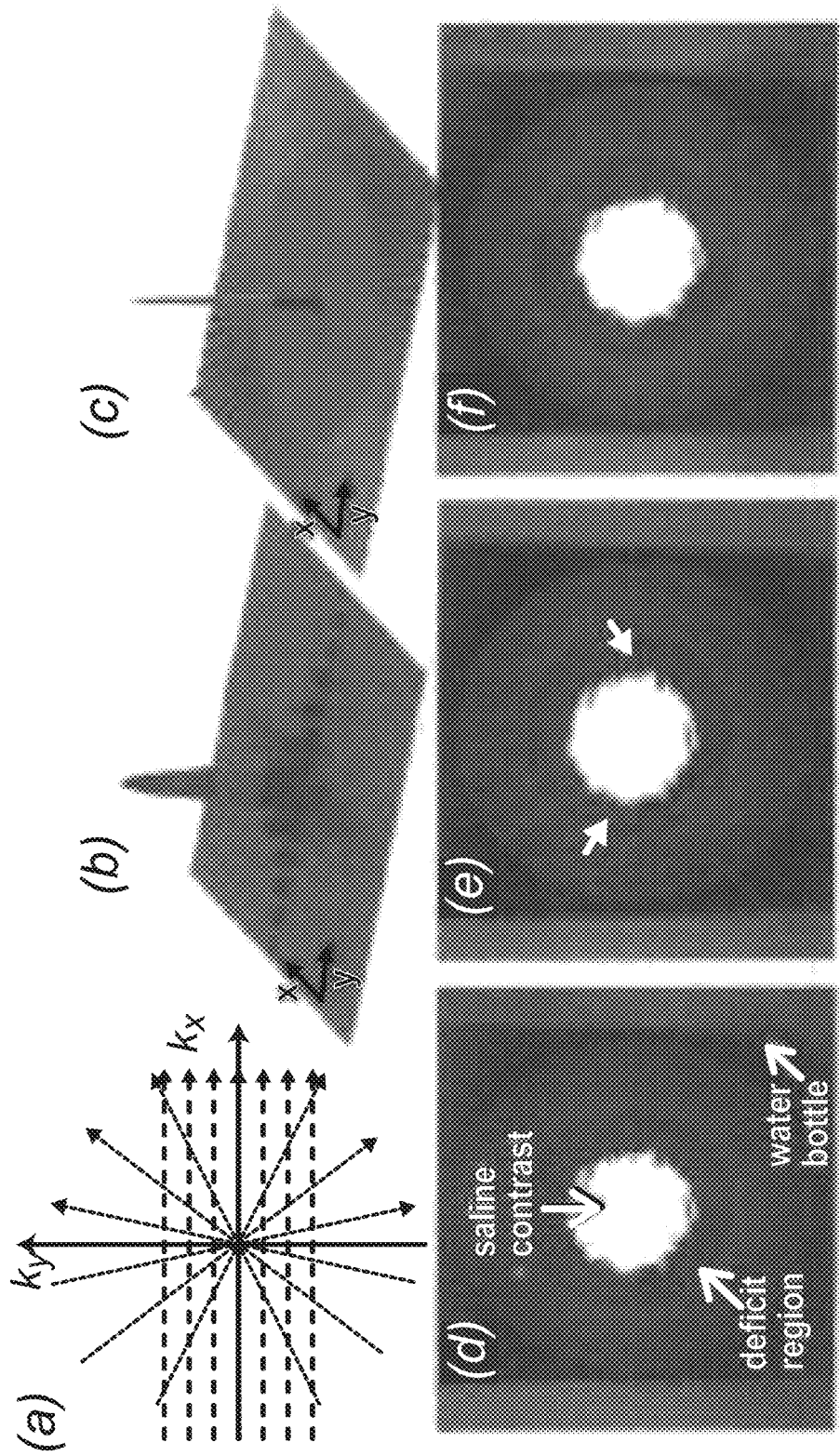
FIG. 1 demonstrates, in accordance with an embodiment of the invention, (a) Cartesian and radial k-space sampling patterns with the same number of readouts and readout resolution; (b) corresponding point-spread function (absolute value of the PSF) in image domain for Cartesian acquisition; (c) PSF For radial acquisition. Insufficient k-space coverage along Ky (phase-encode direction) results in significant ringing along y, as shown in (b). Panels (d)-(f) show reconstructions of an MR gelatin-Gadolinium phantom with realistic signal intensity ratios, demonstrating robustness of projection imaging to Gibbs ringing; (d) fully sampled (ground truth) image with 1×1 mm resolution (384×384 matrix); (e) Cartesian imaging with 108 phase-encodes (arrows point to DRA); (f) radial imaging with 108 projections (no DRAs, mild streaking).

All references cited herein are incorporated by reference in their entirety as though fully set forth. Unless defined otherwise, technical and scientific terms used herein have the same meaning as commonly understood by one of ordinary skill in the art to which this invention belongs. Westbrook et al., *MRI in Practice* 4$^{th}$ ed., and Guyton and Hall, *Textbook of Medical Physiology* 12$^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions," "disease conditions," and "cardiovascular conditions," as used herein, may include but are in no way limited to coronary artery disease (CAD), as well as other conditions associated with perfusion defects and/or wall motion abnormalities of the heart.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

The inventors have developed a novel high-resolution cardiac magnetic resonance (CMR) perfusion technique that eliminates the need for ECG gating or synchronization altogether. The present invention offers several improvements over prior methods, including: (1) continuous uninterrupted acquisition without any ECG/cardiac gating or synchronization that achieves the required image contrast for imaging perfusion defects; (2) an accelerated image reconstruction technique that is tailored to the data acquisition scheme and eliminates/minimizes dark-rim image artifacts; and (3) concurrent imaging of perfusion and myocardial wall motion (cardiac function), which in certain cases can eliminate the need for a separate assessment of cardiac function (hence shortening overall exam time), and/or provide complementary diagnostic information in CAD patients. A number of detailed embodiments of the invention are described herein below.

In various embodiments, the invention teaches a method for eliminating dark-rim artifacts in first-pass myocardial perfusion imaging. In some embodiments, the method includes using an MRI machine to apply a pulse sequence with radial k-space sampling to a volume of interest (VOI) in a subject, wherein the VOI includes a region of the subject's heart. In some embodiments, the method includes using a model-based/iterative reconstruction technique (such as those described in the examples herein below) to generate one or more images of one or more slices or VOIs within the heart region in the subject. In some embodiments, imaging parameters include: FOV read=270-350 mm; BW~800 Hz/pixel; flip angle=12°; TR=2.4-2.6 ms; TI=100 ms. In some embodiments, the scan is accelerated using the parallel imaging method of SENSE (as described in greater detail herein) with 48-56 readouts per frame. In some embodiments, a 3T scanner is used. One of skill in the art would readily appreciate that certain imaging parameters could be adjusted while still effectively imaging a region of the heart within the VOI. Merely by way of example, BW could be from 600 to 1400 Hz/pixel. The flip angle could be from 12 to 30 degrees, TR could be 2.0 to 3.5 ms, TI could be 80 to 160 ms. In some embodiments, the scanner used could be a 1.5T scanner. In some embodiments, a Siemens Verio scanner is used. In some embodiments, the method further includes introducing a contrast agent into the subject's vascular system prior to or during imaging. Merely by way of non-limiting examples, contrast agents that could be used include any Gadolinium-based contrast agent with T1-shortening effects such as Optimark or Magnevist. In some embodiments, the images generated depict the heart within 30 to 60 heartbeats after initial LV contrast uptake.

In various embodiments, the invention teaches a method for ungated cine first-pass CMR for concurrent imaging of myocardial perfusion defects and wall motion abnormalities. In some embodiments, first-pass perfusion (FPP) data is acquired on a 3T scanner by applying an ungated RF-spoiled gradient recalled echo (GRE) sequence with continuous golden-angle radial acquisition of 1 slice (called "cine FPP") within a VOI in a subject, wherein the VOI includes a region of the subject's heart. In certain embodiments, imaging parameters include: resolution ~1.5×1.5×6 mm; 30 sec scan; 13,000 projections; flip=14°. In some embodiments, image reconstruction is performed using a regularized iterative SENSE scheme. In some embodiments, temporal resolution is 61 ms. One of skill in the art would appreciate that certain imaging parameters could be modified without substantially diminishing the improvements offered by the inventive method. Merely by way of example, the scan duration could be from 30 to 60 sec. Projections could range from 3000 to 15000 per slice or volume. In addition, the flip angle could vary from 12 to 30 degrees. In some embodiments, temporal resolution could be from 40 to 400 ms. In some embodiments, the method further includes introducing a contrast agent into the subject's vascular system prior to or during imaging. Merely by way of non-limiting examples, contrast agents that could be used include any Gadolinium-based contrast agent with T1-shortening effects such as Optimark or Magnevist. In some embodiments, the method further includes diagnosing the subject with the presence or absence of a condition associated with a perfusion defect and/or a wall motion abnormality, based upon one or more of the images generated.

In some embodiments, the invention teaches a method for real-time FPP myocardial MRI using ungated magnetization-driven radial sampling. In some embodiments, the method includes (1) using an MRI machine to apply an ungated T1-weighted RF-spoiled GRE pulse sequence with continuous golden-angle radial sampling to a volume of interest (VOI) in a subject, wherein the VOI includes a region of the subject's heart, and wherein the T1-weighting and contrast properties of the sequence are magnetization-driven, and (2) using a sliding window scheme (as described herein below and in the examples) to generate one or more images of one or more anatomical structures within the VOI. In some embodiments, the method further includes introducing a contrast agent into the subject's vascular system prior to or during imaging. In some embodiments, the method further includes diagnosing the subject with the presence or absence of a condition associated with a perfusion defect, based upon one or more of the images generated. In some embodiments, FPP data is acquired using the sequence of FIG. 5b, with continuous ungated radial acquisition of a short-axis slice at mid ventricle. In some embodiments, the following imaging parameters are used: FA=14°, acquired in-plane resolution=1.4×1.4 mm² with readout FOV=270 mm and 192 samples per readout, slice thickness=6 mm, continuous acquisition of 12,500 projections during 31 seconds, TR/TE=2.5/1.3 ms, rBW~1370 Hz/pixel. In some embodiments, the pulse sequence includes gradient-delay correction (prospectively optimized for the scanner). In some embodiments, the acquisition of the radial spokes is interleaved, based on the golden-angle scheme (as described in the "examples" section). In some embodiments, image reconstruction parameters are selected based on a representative dataset. One of skill in the art would readily appreciate that certain imaging parameters relevant to the methods of this section could be modified without substantially altering the results. In some embodiments, the FA is from 12 to 30 degrees. In some embodiments, slice thickness is from 6 mm to 10 mm. In certain embodiments, continuous acquisition is of from 3000 to 15000 projections (per slice or per slab) during 30 to 60 seconds and TR/TE ranges from 2.0/1.0 ms to 3.5/2.0 ms. In some embodiments rBW is from 600 to 1400 Hz/pixel.

With respect to image reconstruction, in some embodiments a sliding window of between 40 to 400 ms temporal shifts is applied to reconstruct 1 to 25 frames per second (per slice or slab). In some embodiments, 1 slice imaging is performed at 3T and TR=2.5 ms. Optional image reconstruction schemes are further disclosed in the examples and experiments set forth herein.

One of skill in the art would readily appreciate that several different types of imaging systems could be used to perform the inventive methods described herein, including all of the types of imaging systems described in the examples and experiments set forth herein, as well as similar systems.

Figure 10:
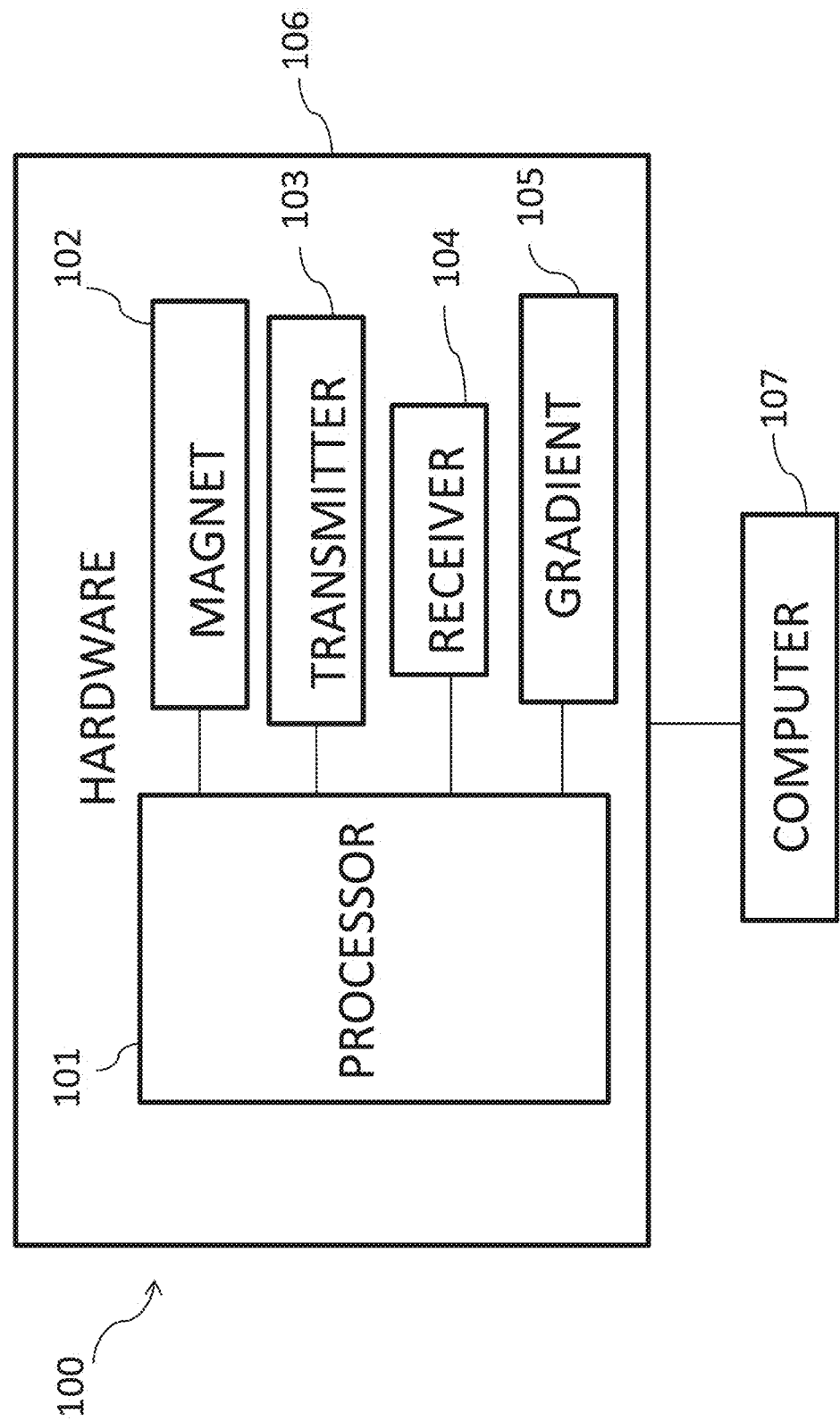
FIG. 10 depicts a system in accordance with an embodiment of the invention.

Further, by way of non-limiting example, FIG. 10 depicts a view of a system 100 that can be used to accomplish the inventive methods. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil. Hardware 106 includes gradient 105. Gradient 105 can represent one or more coils used to apply a gradient for localization.

Processor 101, in communication with various elements of hardware 106, includes one or more processors configured to implement a set of instructions corresponding to any of the methods disclosed herein. Processor 101 can be configured to implement a set of instructions (stored in a memory of hardware 106) to provide RF excitation and gradients and receive magnetic resonance data from a volume of interest.

Computer 107 is coupled to hardware 106. Computer 107 can include one or more of a desktop computer, a workstation, a server, or a laptop computer. In one example, computer 107 is user-operable and includes a display, a printer, a network interface or other hardware to enable an operator to control operation of the system 100.

In various embodiments, the invention further teaches a non-transitory machine-readable medium having machine executable instructions for causing one or more processors of a magnetic resonance imaging (MRI) machine (such as those described herein) to execute a method, including (1) applying the pulse sequence of any of the embodiments described herein to a volume of interest (VOI) in a subject, wherein the VOI includes a region of the subject's heart; (2) acquiring magnetic resonance data from the volume of interest (VOI) in the subject; and (3) generating one or more images based on the magnetic resonance data using an image generating (reconstruction) method described herein.

One skilled in the art will recognize many methods and materials similar or equivalent to those described herein, which could be used in the practice of the present invention. Indeed, the present invention is in no way limited to the methods and materials described.

EXAMPLES

Example 1

Experiments I

Eliminating Dark-Rim Artifacts in First-Pass Myocardial Perfusion Imaging

Background

The inventors' experiments demonstrate that projection imaging significantly reduces the prevalence and spatial extent of subendocardial dark-rim artifacts (DRAs) in first-pass perfusion (FPP) myocardial MR, compared to conventional Cartesian techniques. A major cause of DRAs, which remain a major concern in FPP imaging, is known to be the so called Gibbs ringing (truncation) phenomenon. Radial k-space sampling exhibits minimal Gibbs effects with typical FPP parameters, thereby eliminating a major contributing factor to DRAs. The underlying principles are demonstrated in FIG. 1, which describes Cartesian and radial k-space sampling (with the same number of readouts) and the corresponding point spread functions (PSFs). Insufficient coverage along the phase-encode direction with Cartesian sampling results in significant ringing in the image domain (FIG. 1b). In contrast, angular under-sampling results in streaks outside of a "local" region for radial images (FIG. 1c). Panels 1d-f of FIG. 1 show phantom studies (gelatin-based with realistic contrast ratios, resembling the LV with a deficit region) verifying the described PSF effects.

Methods

Healthy human volunteers (N=12) were imaged on a 3T scanner (Siemens Verio). Two FPP scans (SR-prepared FLASH) were performed at rest (>10 minutes gap) using a single-shot radial pulse sequence followed by a single shot Cartesian sequence (common parameters: FOV read=270-350 mm; BW about 800 Hz/pixel; flip angle=12'; TR=2.4-2.6 ms; TI=100 rns). Both scans were accelerated using rate 2 parallel imaging (TGRAPPA for Cartesian and SENSE for radial) and the number of readouts per frame was matched within 10% (range: 48-56). Scans were visually read for artifact by 2 expert readers blinded to the study protocol using a consensus 0-4 scoring scheme (0: no DRA; 4: severe DRA).

Results

Figure 2:
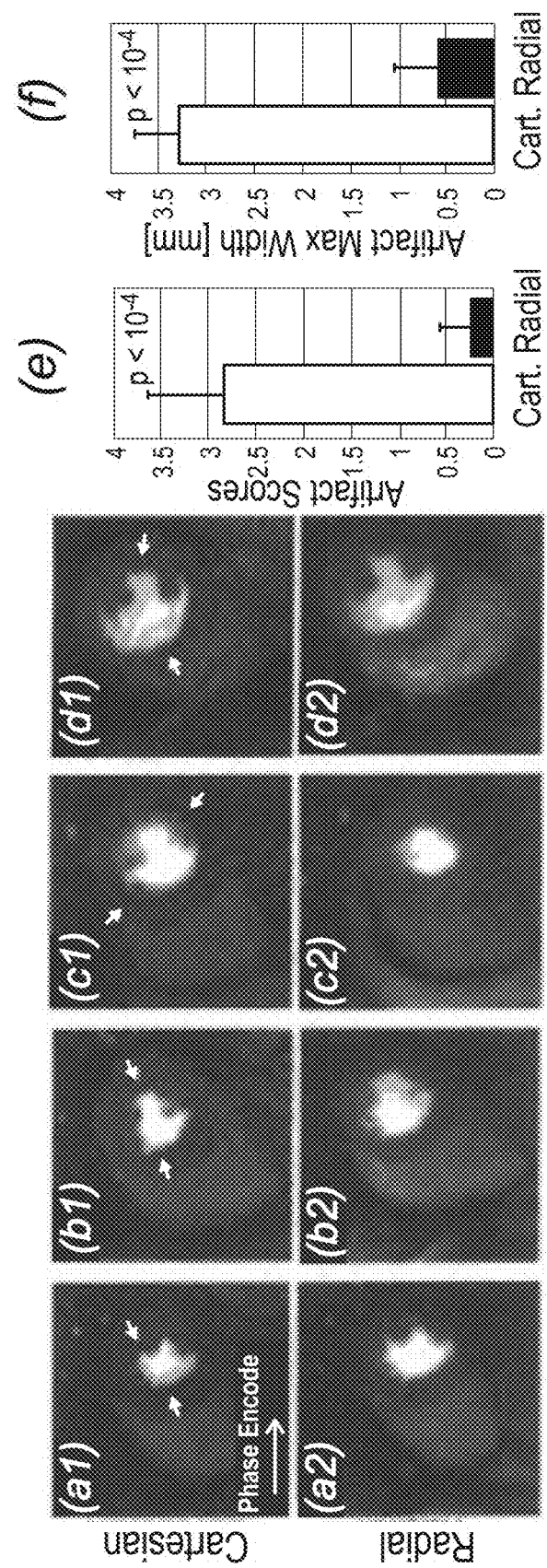
FIG. 2 demonstrates, in accordance with an embodiment of the invention, representative first-pass CMR perfusion images from 4 of the 12 studied healthy humans: top panels (a1) to (d1) show Cartesian images (arrows point to DRAs); bottom panels (a2) to (d2) show the corresponding radial images. All images correspond to similar early myocardial enhancement phase (7 heart beats after initial LV contrast uptake). Panel (e) shows summary of artifact scores assigned by two expert readers (consensus 0-4 scale scoring, 0: no DRA, 4: severe DRA). Panel (f) shows the maximum measured width of the artifact (along polar directions).

Representative images from 4 of the 12 studied subjects are shown in FIG. 2, where the top panels show Cartesian images (arrows point to DRAs) and bottom ones are the corresponding radial images. All images correspond to a pre-defined early myocardial enhancement phase as indicated in the above description of FIG. 2. Qualitative analysis (FIG. 2e) clearly shows the superiority of radial imaging in reducing the DRA. Similar findings were evident from quantitative assessment of the DRA maximal width (FIG. 2f).

Conclusions

The inventors demonstrated herein that radial imaging is capable of significantly reducing the dark rim artifact even in the early myocardial enhancement phase of a first-pass perfusion image series, due to its inherent robustness to Gibbs ringing. Such artifacts may confound interpretation and diagnosis of subendocardial perfusion defects (which may "fill in" early during the myocardial enhancement phase). Advanced (e.g., model-based/iterative) reconstruction techniques (as described herein) with radial acquisition can be used to improve image quality while preserving the described dark-rim-minimizing properties.

Example 2

Experiments II

Ungated Cine First-Pass CMR for Concurrent Imaging of Myocardial Perfusion Defects and Wall Motion Abnormalities Background Combined assessment of wall motion from cine imaging and perfusion defects from first-pass perfusion (FPP) imaging has been shown to have high diagnostic performance for detection of acute ischemia. In this setting, a single ungated CMR scan capable of simultaneously capturing perfusion deficits and wall motion abnormality can be useful for rapid diagnosis of ongoing acute ischemia. Described herein is an accelerated FPP technique with ungated continuous acquisition capable of generating cardiac-phase resolved FPP images, thereby enabling concurrent imaging of wall motion and perfusion deficits.

Methods

FPP imaging without magnetization preparation using a steady state acquisition has been described before and seen recent interest, wherein the focus has been on acquiring one image during the quiescent phase. Canines with reversible ischemia were studied (N=5; >90% LAD stenosis for 4, no stenosis for 1). Resting FPP data was acquired on a 3T scanner (Siemens Verio) using an ungated RF-spoiled GRE sequence with continuous golden-angle radial acquisition of 1 slice (called "cine FPP"; resolution: 1.5×1.5×6 mm, 30 sec scan, 13,000 projections, flip=14°). All scans were performed 7±2 minutes post occlusion and the mean heart rate (HR) was 98 bpm. Image reconstruction was performed using a regularized iterative SENSE scheme (temporal resolution: 61 ms). For comparison, a conventional gated SR-prepared FLASH "standard FPP" scan was also acquired.

Results

Figure 3:
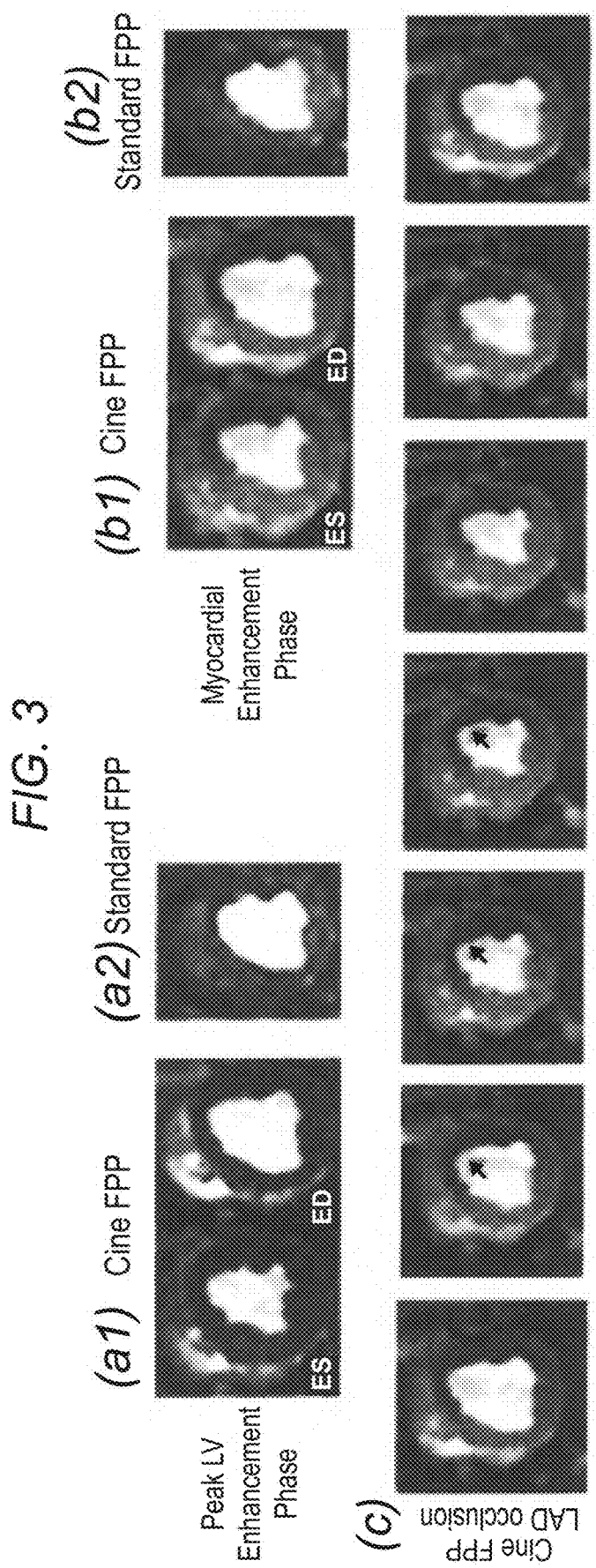
FIG. 3 demonstrates, in accordance with an embodiment of the invention, panels (a1) and (b1) show cine FPP images (systolic and diastolic phases) in two different contrast enhancement phases: peak LV bloodpool enhancement; and myocardial enhancement. Panels (a2) and (b2) show the corresponding images from the standard FPP scan. Row (c) shows 7 frames (frame rate: 16 frames/s) from one heartbeat of the ungated cine FPP images during myocardial enhancement. Arrows point to the hypokinetic wall.
Figure 4:
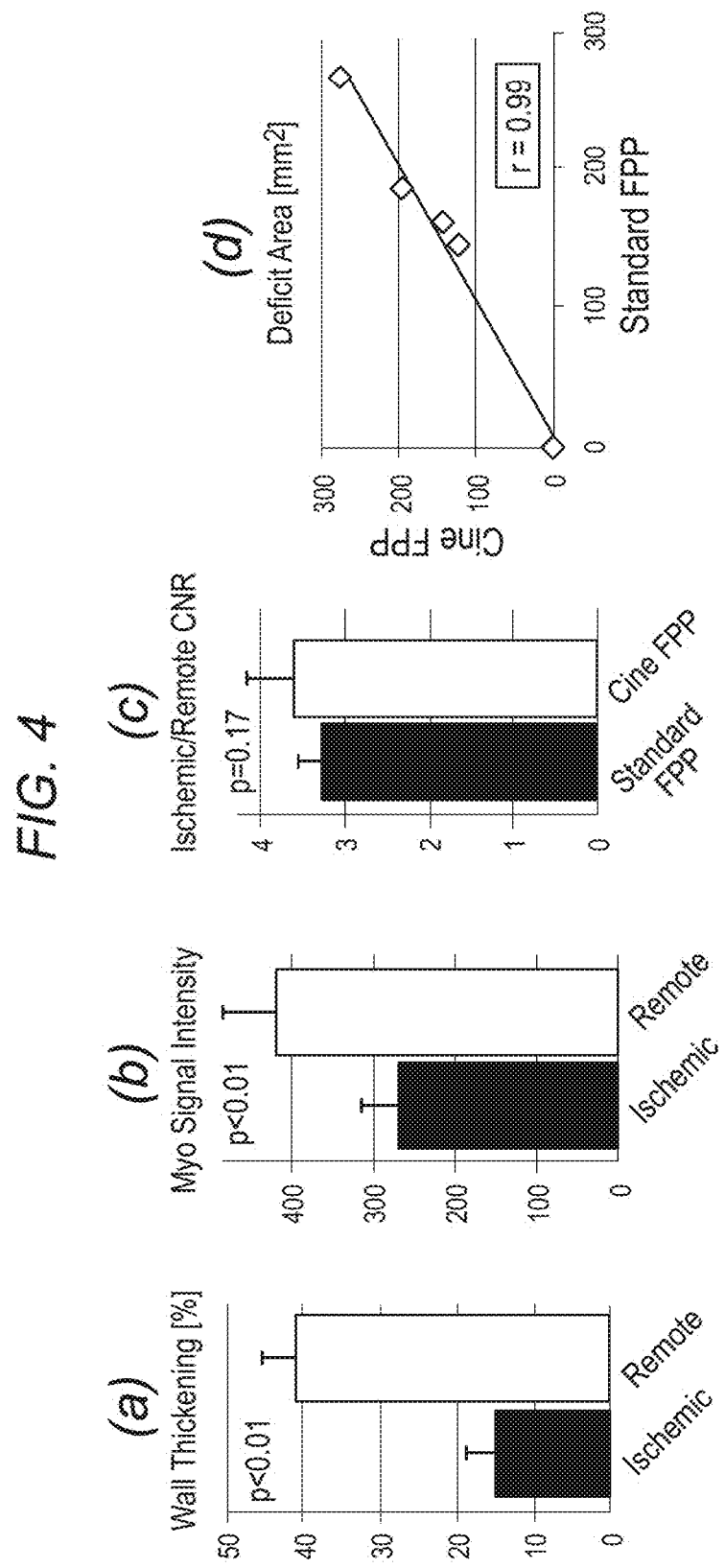
FIG. 4 depicts, in accordance with an embodiment of the invention, panels (a) and (b) show the results of wall motion (systolic wall thickening as a percentage of diastolic thickness) and myocardial signal intensity from the cine FPP images in 4 ischemic dogs. For (a), consecutive frames from peak LV enhancement and for (b) a diastolic frame during myocardial enhancement phase were analyzed. Panel (c) compares the ischemic-to-remote myocardial image contrast (for the 4 ischemic dogs) of the cine FPP images to standard FPP (SR-prepared ECG-gated FLASH), which shows that cine FPP has slightly higher CNR (3.6 vs. 3.3, statistically insignificant). Finally, (d) compares the detected deficit area (in $mm^2$) between cine and standard FPP in all 5 studied dogs (1 with no occlusion), which shows a very good correlation (r=0.99).

The top row of FIG. 3 shows cine FPP images (systolic/diastolic) in peak LV and myocardial enhancement phases, along with the corresponding images from the standard FPP scan. FIG. 3(C) shows 7 frames (16 frames/s) from the cine FPP in the myocardial enhancement phase. Arrows point to hypokinesia. FIGS. 4(A)-(B) show the result of wall motion and myocardial signal intensity analysis from the cine FPP images. FIG. 4(C) compares the myocardial contrast properties of the cine FPP images to standard FPP, showing similar ischemic-to-remote CNR. Finally, 4(D) compares the detected deficit area between cine and standard FPP, showing a positive correlation (r=0.99).

Conclusions

The inventors have demonstrated, for the first time, the feasibility and effectiveness of ungated cardiac-phase resolved (cine) FPP imaging for concurrent imaging of myocardial wall motion and perfusion in an animal model with flow-limiting stenosis. The inventive method improves the feasibility of detecting acute myocardial ischemia using CMR because of its reduced scan time (single scan for both cine and FPP) and reduced complexity (no cardiac gating). It also enhances the accuracy and speed of diagnosis by virtue of concurrent (inherently fused) imaging of wall motion and FPP. The results demonstrate that the inventive method is capable of imaging at high heart rates with high spatial and sufficient temporal resolution. While the current method is focused on imaging a single slice during a breathhold, one of skill in the art would appreciate that it can be extended to 3D through spatio-temporal acceleration.

Example 3

Experiments III

Real-Time First-Pass Perfusion Myocardial MRI Using Ungated Magnetization-Driven Radial Sampling Overview As described herein below, another aspect of the invention involves establishing an ungated first-pass perfusion (FPP) cardiac MRI (CMR) technique that improves accessibility and diagnostic capability of perfusion CMR in clinical practice. The inventors studied the effectiveness of a real-time FPP imaging technique using ungated magnetization-driven acquisition employing radial sampling.

An ungated T1-weighted pulse sequence with continuous 2D golden-angle radial sampling was developed by the inventors for FPP imaging. The flip angle was optimized using simulations to achieve maximum contrast-to-noise ratio (CNR) between hypoperfused and normal myocardium. A sliding-window scheme was used to enable reconstruction of 8 real-time frames per second. Canines (n=5) were imaged at 3T with and without coronary stenosis and FPP data was acquired using the real-time scheme and a conventional ECG-gated method.

The inventors' studies, demonstrated in greater detail below, indicate that their real-time method is capable of generating high-resolution ($1.7 \times 1.7 \times 6$ mm$^3$) artifact-free FPP images without the need for gating in the setting of ischemia and at high heart rates (92±21 beats/minute), while matching the performance of conventional FPP imaging in terms of hypoperfused-to-normal myocardial CNR (real-time: 5.18±0.70; gated: 4.88±0.43). Furthermore, the detected perfusion defect areas in the real-time images are consistent with the conventional FPP images.

Overall, the inventors demonstrate that real-time magnetization-driven ungated imaging with continuous radial sampling is a very useful method for myocardial perfusion MRI.

Introduction

As indicated above, first-pass perfusion (FPP) myocardial MRI is a promising method for accurate diagnosis of coronary artery disease (CAD). Despite significant technical advances, persistent problems have limited the widespread use of myocardial MRI as a modality for routine diagnosis of CAD. One problem is that cardiac MRI (CMR) is generally considered to be a more complex method compared to nuclear myocardial perfusion imaging and more dependent on the expertise of the technologist/operator. Hence, simplification and streamlining of the FPP protocol would increase its accessibility for examining patients with known or suspected CAD.

A major limitation and source of complexity in FPP imaging is the need for near-perfect electrocardiographic (ECG) gating during stress and rest scans. Specifically, the increase in heart rate (HR) variability during vasodilator stress FPP scans can lead to missed slice acquisitions and therefore result in loss of diagnostic information during the short peak-hyperemic time window. Such effects are compounded in arrhythmic patients, for whom even rest perfusion imaging can be quite difficult using gated methods. Moreover, reliable ECG gating can be challenging at high fields (e.g., 3T) owing to the amplified magneto-hydrodynamic effects. Hence, the need for ECG gating not only increases the overall complexity of the imaging protocol, but also may reduce the clinical utility and diagnostic performance of FPP imaging. Ungated CMR methods eliminate the need for ECG gating or other forms of cardiac synchronization, and will help reduce the workflow complexity associated with FPP exams.

As demonstrated herein, the inventors have developed and tested a "real-time" FPP imaging scheme using an ungated magnetization-driven RF-spoiled GRE pulse sequence with continuous golden-angle radial sampling of a 2D slice. In the context of real-time CMR, the required frame rate depends on the type of motion being resolved and can range from 7 frames/s to 17 frames/s or higher. High frame rates (≈20 frames/s) are required to accurately resolve cardiac motion in real time; such strict temporal resolution demands are not needed in perfusion CMR. In some embodiments, this inventive method is referred to as real-time FPP imaging since: (i) the acquisition is ungated and continuous; (ii) the method generates multiple temporally-contiguous FPP images of the same slice per second (rate: 8 frames/s); and (iii) the reconstruction is performed without data-sharing between different R-R intervals—eliminating the possibility of temporal smoothing or filtering effects, which may reduce the temporal fidelity of a FPP image series. As demonstrate herein, the inventors evaluated the contrast properties and effectiveness of the real-time scheme relative to the conventional (SR-prepared ECG-gated) acquisition in an animal model with coronary artery stenosis.

Methods

Real-Time Pulse Sequence

Figure 5:
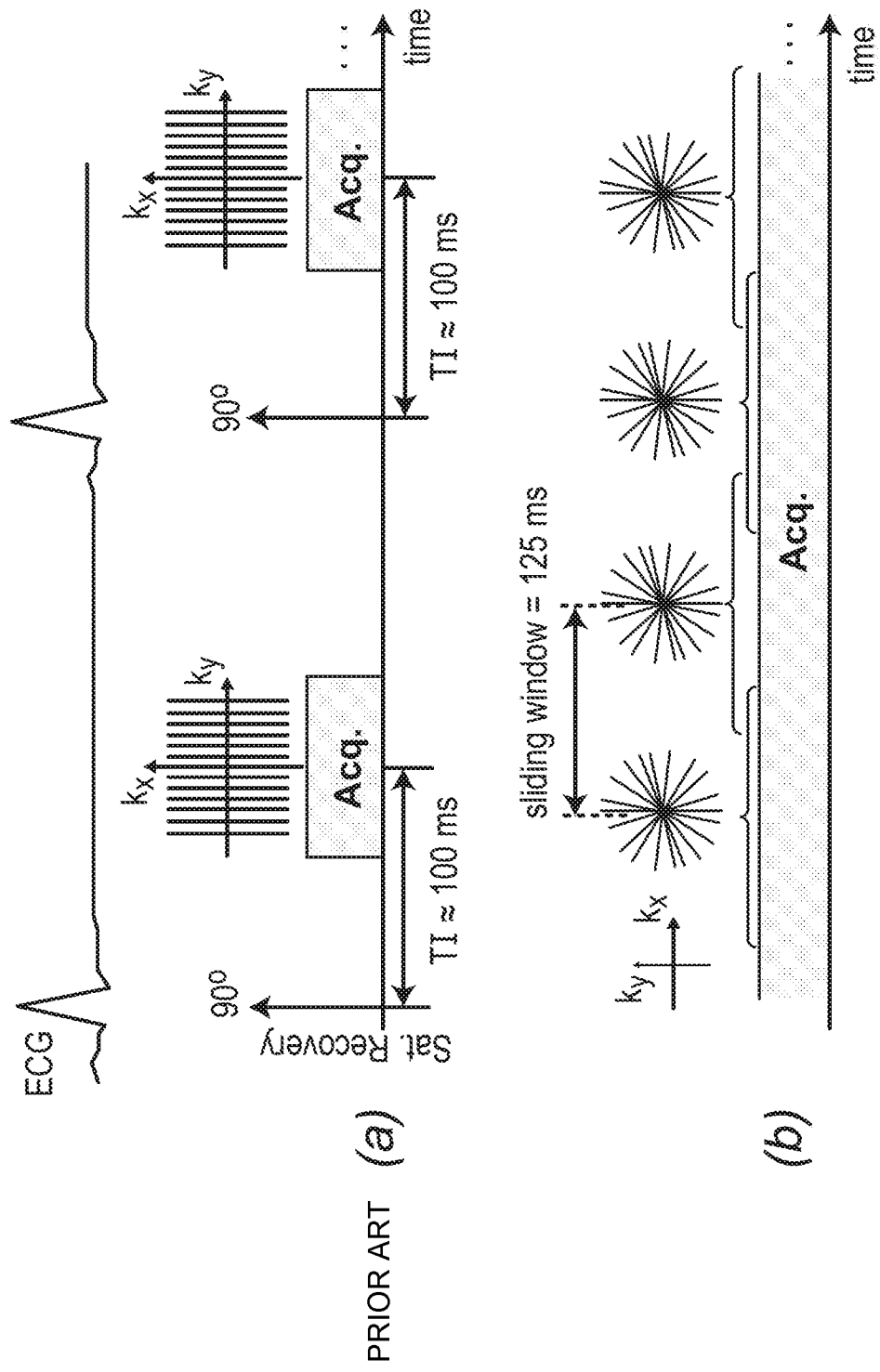
FIG. 5 depicts, in accordance with an embodiment of the invention, a description of the gated (conventional) and inventive real-time first-pass perfusion pulse sequences. (a) Conventional pulse sequence: ECG gated FLASH with saturation recovery (SR) magnetization preparation; typically, an undersampled Cartesian k-space is acquired (reconstructed using parallel imaging), synchronize with the ECG gating signal at a pre-defined TI time (e.g. 100 ms). (b) Inventive real-time pulse sequence: ungated FLASH (optimized for flip angle) with continuous acquisition of a 2D golden-angle radial k-space trajectory (111.246° angular spacing between consecutive projections). A sliding window (125 ms temporal shifts) is applied to reconstruct one frame from consecutive projections resulting in 8 real-time frames per second. No external ECG signal or other forms of cardiac synchronization is needed for this method.

Conventional FPP pulse sequences are ECG-gated and include an SR magnetization preparation prior to acquisition of each slice, in most cases acquired using GRE readouts as shown in FIG. 5(a). Typically, an undersampled Cartesian k-space is acquired (reconstructed using parallel imaging), and synchronized with the ECG gating signal at a pre-defined TI time ($\approx$100 ms). The relevant inventive real-time pulse sequence, depicted in FIG. 5(b), is an ungated fast low angle shot (FLASH) acquisition (RF-spoiled GRE with 50° quadratic RF phase increments) with golden-angle radial k-space trajectory. The T1-weighting and contrast properties of the sequence are magnetization-driven, i.e., the T1 contrast is provided by the approximate steady state magnetization. On the reconstruction side, a sliding window (125 ms temporal shifts) is applied to reconstruct 8 frames per second. Radial sampling is used because of its resilience to undersampling and cardiac motion. In addition, high-resolution golden-angle acquisition enables retrospective adjustment of spatial/temporal resolution (further described in the section below regarding image reconstruction). Thanks to this feature, besides eliminating the need for ECG setup/gating, the method further simplifies the MRI procedure by eliminating the need for choosing/checking the acquisition parameters before the FPP scan.

The choice of the flip angle (FA) is important for obtaining a desirable myocardial contrast-to-noise ratio (CNR). The inventors used numerical simulations to identify the optimal FA for the proposed pulse sequence. Since the diagnostic task in FPP imaging is to delineate normal and hypoperfused myocardium, their goal in optimizing the FA was to maximize the hypoperfused-to-normal myocardial CNR, hereafter dubbed "perfusion CNR" (pCNR). Unlike previous methods which use the fixed pre-contrast T1 in place of the T1 value for hypoperfused myocardium, the inventors' optimization was aimed at maximizing the pCNR for a wide range of normal and hypoperfused myocardial T1s encountered in a FPP scan. While not wishing to be limited by any one particular theory, the inventors' results strongly indicate that $\alpha$=14° is a near optimal FA for achieving the best pCNR for 1-slice imaging at 3T (TR=2.5 ms).

Imaging Experiments

A total of 5 canines were imaged on a 3T clinical scanner (Magnetom Verio, Siemens Healthcare, Erlangen, Germany) with a standard cardiac-torso receiver coil array. Imaging experiments were done under a protocol approved by the Institutional Animal Care and Usage Committee at Cedars-Sinai Medical Center (CSMC). A left thoracotomy was performed and catheters were inserted into the descending aorta and both atria, and were routed through the chest cavity to exit the body. A hydraulic occluder was positioned around the left anterior descending (LAD) artery, and a Doppler flow probe was placed distal to the occluder (both were MR compatible). Animals were allowed to recover for 7 days prior to the imaging studies. On the day of MRI studies, dogs were fasted, sedated, intubated, and anesthetized and placed on the scanner table. Animals were ventilated and positioned on the scanner table in a feet-first right-anterior oblique position. Continuous physiological monitoring and coronary Doppler flow was performed for the entire the imaging session.

In 4 of the 5 dogs, severe LAD stenosis was inflicted within the MR scanner by inflating the hydraulic occluder, inducing reversible ischemia; the extent of stenosis was confirmed based on Doppler flow velocities. One of the dogs was used as control, i.e., was imaged with no stenosis. Resting FPP data was acquired using the relevant real-time sequence (FIG. 5(b)) during a $\approx$30 second breathhold; for comparison, a conventional gated FPP scan (SR-prepared FLASH) was also acquired, here referred to as "gated FPP." The contrast injection dose (gadoversetamide/Optimark, Mallinckrodt Inc., Hazelwood, Mo., USA) for each perfusion scan was 0.05 mmol/kg with a 14-17 minute time gap in between the two scans to allow for contrast wash out (verified using a TI scout). Each scan was performed 7±2 minutes post stenosis (same level based on Doppler; released after each scan). Delayed enhancement imaging was performed to rule out infarction at the end of the imaging study.

Resting FPP data was acquired using the real-time sequence with continuous ungated radial acquisition of a short-axis slice at mid ventricle with the following parameters: FA=14° (as described above), acquired in-plane resolution=1.4×1.4 mm$^2$ with readout FOV=270 mm and 192 samples per readout, slice thickness=6 mm, continuous acquisition of 12,500 projections during 31 seconds, TR/TE=2.5/1.3 ms, rBW$\approx$1370 Hz/pixel. The pulse sequence included gradient-delay correction (prospectively optimized for the scanner as described in Peters D C et al. Centering the projection reconstruction trajectory: Reducing gradient delay errors. Magn. Reson. Med. 2003; 50:1-6, which is incorporated herein by reference in its entirety), and acquisition of the radial spokes were interleaved based on the golden-angle scheme, as described in Winkelmann et al. An optimal radial profile order based on the Golden Ratio for time-resolved MRI. IEEE Trans. Med. Imaging 2007; 26:68-76, which is incorporated herein by reference its entirety. The parameters for the gated scan were as follows: SR-prepared FLASH with TI=100-120 ms, FA=12°, in-plane resolution=2.4×1.8 mm$^2$, slice thickness=6 mm, readout FOV=295 mm, rBW$\approx$650 Hz per pixel, TR/TE=2.5/1.3 ms; 2-3 slices per heartbeat; TGRAPPA rate 2. The average HR for the control animal was 57 beats per minute (bpm) and 92±21 bpm for the ischemic animals during the real-time scans (rest imaging).

Image Reconstruction

Figure 6:
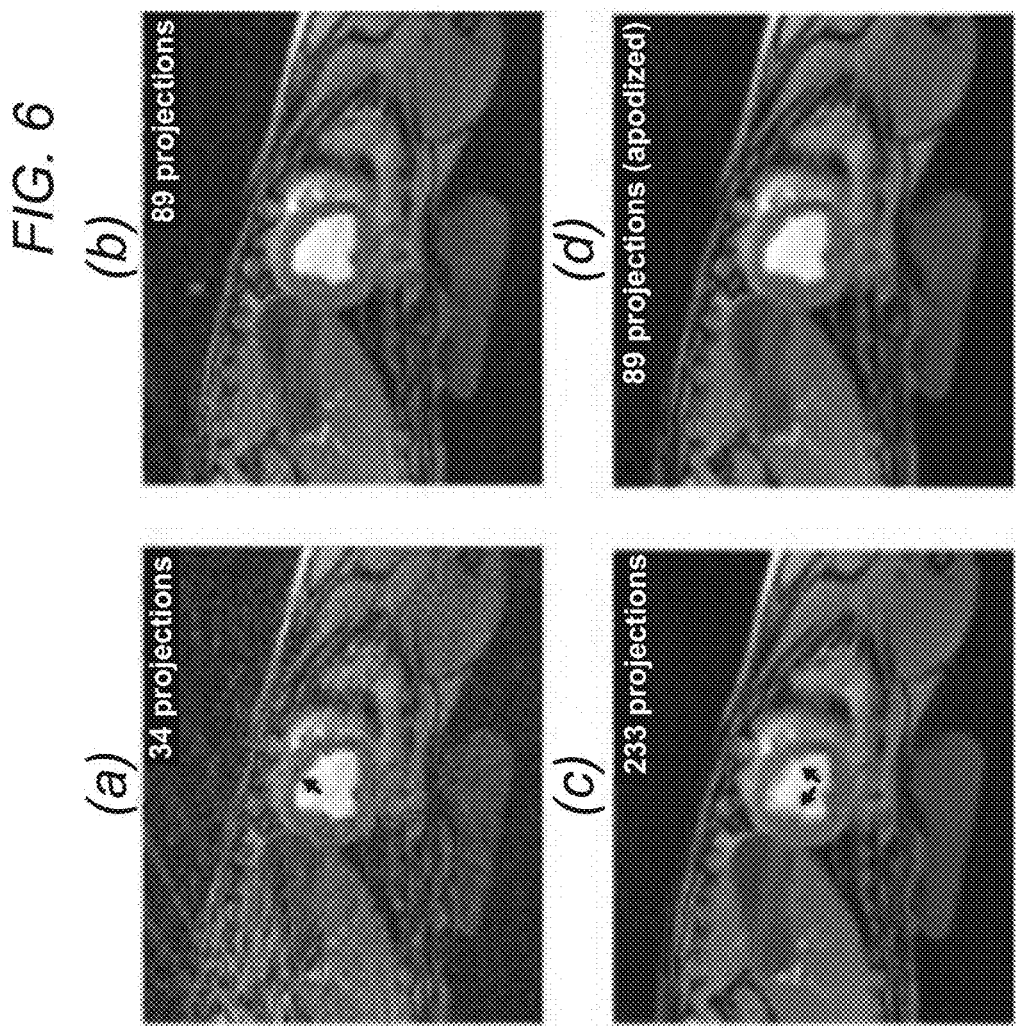
FIG. 6 depicts, in accordance with an embodiment of the invention, a demonstration of the methodology for retrospective selection of reconstruction parameters using the properties of golden-angle radial acquisition: all images correspond to a similar time-point in the real-time FPP scan (diastole, 10 seconds after start of the scan, prior to myocardial enhancement) in one of the ischemic dog studies (heart rate: 98 bpm). (a,b,c): Standard regridding (ramp-shaped density-compensation function) with 34, 89, and 233 projections, respectively (same gray-scale; in-plane resolution: 1.4×1.4 $mm^2$); the arrows in (a)-(b) point to streaking artifacts in the myocardium and outside of the heart region, and those in (c) point to blurring at the endocardial wall caused by the large temporal window (582 ms). (d): Apodized regridding reconstruction using a Gaussian kernel as the apodizing function. The SNR (ratio of mean to standard deviation of signal intensity in the septum) for (a)-(d) are 3.6, 8.7, 15.1, and 14.9, respectively. (e) Demonstration of the effect of apodization on the reconstruction resolution; the plot shows 1D cut out of the main lobe of the point spread function (PSF) corresponding to the reconstructions in (b) and (d). This plot only shows a fraction of the central region of the PSFs to allow for visualization of the FWHM differences. The ratio of the FWHM for (d) relative to (b) is 1.2, which implies an in-plane resolution of 1.7×1.7 mm$^2$ for the apodized reconstruction in (d). Comparing (b) and (d), apodization results in improved SNR (reduced streaking) at the cost of spatial resolution (1.2-fold widening of FHWM as shown in (e)): nevertheless, the reconstructed resolution after apodization (1.7×1.7 mm$^2$) in (d) is significantly higher than conventional FPP methods.

An important advantage of data acquisition using the golden-angle radial trajectory is the possibility of retrospective selection of reconstruction parameters for balancing the temporal/spatial resolution trade-off. In the context of real-time FPP imaging, as described herein, the parameter to select is the number of projections used for regridding in reconstructing each frame (FIG. 5b) and the trade-off is between streaking artifacts (caused by angular undersampling) and image blurring (caused by cardiac motion). One approach to optimize this trade-off, which was adopted by the inventors, is to select the reconstruction parameters based a representative dataset. As shown in FIGS. 6(a-c), the inventors used the dataset from one of the ischemic dog studies (HR$\approx$100 bpm) to visually assess the reconstructed image quality corresponding to several choices of the number of projections (limited to Fibonacci numbers as describe in Winkelmann et al. An optimal radial profile order based on the Golden Ratio for time-resolved MRI. IEEE Trans. Med. Imaging 2007; 26:68-76, which is incorporated herein by reference in its entirety). As described in the FIG. 6, 89 projections (panel b) resulted in a sharp image (clear delineation of the subendocardial border) but with a moderate SNR ($\approx$8.7) due to streaking artifacts; and, 233 projections (panel c) yielded a relatively high SNR ($\approx$15.1) and almost no noticeable streaking artifacts—but with significant blurring caused by cardiac motion. It's worth noting that, although 89 projections is 3.4-fold undersampled relative to the Nyquist criterion for 192 readout points (assuming uniform azimuthal sampling), the level of streaking in FIG. 6(*b*) is relatively low and therefore the in-plane isotropic resolution is determined by the readout pixel size (=1.4 mm); in fact, higher undersampling factors have been used in for myocardial imaging, as described in Peters et al. Myocardial wall tagging with undersampled projection reconstruction. Magn. Reson. Med. 2001; 45:562-567 and Shankaranarayanan et al. Segmented k-Space and Real-Time Cardiac Cine MR Imaging with Radial Trajectories. Radiology 2001; 221:827-836, both of which are incorporated by reference herein in their entirety.

Nevertheless, it is desirable to reconstruct the real-time frames with a higher SNR than FIG. 6(*b*) and free of artifacts (streaking or ringing) while avoiding motion-induced blurring seen in FIG. 6(*c*).

Apodization (windowing of k-space data) improves SNR at the cost of widening the main lobe of the underlying point spread function (PSF), resulting in reduced resolution which can be quantified and controlled by measuring the full-width-at-half-maximum (FWHM) of the PSF's main lobe. The inventors used apodization as a simple solution towards the above-mentioned reconstruction goal. Specifically, a Gaussian kernel was employed to weight the projection data (as described in Naylor et al. Apodizing functions for Fourier transform spectroscopy. J Opt Soc Am A 2007; 24:3644-3648, which is incorporated by reference in its entirety) along the readout direction, and the degree of apodization (width of the Gaussian) was adjusted to result in a 1.2-fold increase in FWHM (compared to non-apodized reconstruction). This implies a reconstruction resolution of 1.7×1.7 mm$^2$, which—although lower than the acquired resolution—is significantly higher than conventional FPP methods (1.5-times smaller pixel compared to the gated method). In return for the increase in FWHM, the PSF streaking components (as described in Scheffler et al. Reduced circular field-of-view imaging. Magn. Reson. Med. 1998; 40:474-480, which is incorporated herein by reference in its entirety) are significantly attenuated (resulting in improved SNR); specifically, the 2-norm energy and peak amplitude of streaks are reduced by 1.4-fold and 1.9-fold, respectively. As expected, the apodized reconstruction using 89 projections shown in FIG. 6(*d*) achieved high SNR ($\approx$14.9) with significantly reduced streaking compared to 6(*b*). FIG. 6(*e*) verifies the reconstructed resolution based on the FWHM measure. In addition to improving the SNR, this level of apodization effectively eliminates PSF ringing components to preclude ringing-induced artifacts. Based on well-known Fourier transform relationships, the apodization process can be alternatively implemented as a filtering process in the image domain. This can be accomplished by deriving an equivalent Gaussian filtering in the image domain and using a two-dimensional convolution process to apply the filter. Finally, in addition to the Gaussian kernel, there are alternative apodization functions that can be used; specifically, most windowing schemes used in digital signal processing can be employed such as the Hamming window.

The Gaussian kernel, however, has certain optimality properties as described in Naylor et al. Apodizing functions for Fourier transform spectroscopy. J Opt Soc Am A 2007; 24:3644-3648; which is incorporated by reference herein in its entirety.

Image reconstruction for the real-time scan was performed offline on a frame by frame basis by reconstructing multiple images per R-R cycle using a sliding-window. As described above, each frame was reconstructed using 89 readouts (222 ms temporal window) and the sliding window was then shifted by 50 readouts (125 ms) to reconstruct the next frame, resulting in 8 real-time frames/s. The reconstruction procedure was executed on a workstation (Pentium Dual-CPU Xeon 3.3 GHz) in MATLAB (Mathworks, Natick, Mass., USA) using a non-uniform FFT routine (as described in Fessler J A. On NUFFT-based gridding for non-Cartesian MRI. Journal of Magnetic Resonance 2007; 188:191-195, which is incorporated herein by reference in its entirety). With parallel processing (12 cores), the reconstruction time for each frame was about 0.7 s/frame, or a total of 3 minutes per scan. All reconstructed images were converted to DICOM format using tags generated online by the scanner software.

Image Analysis

The first 4 real-time frames were excluded from the image analysis to allow for transition to steady state (corresponding to 200 RF excitations during the initial 500 ms). Image analysis was performed manually using a DICOM viewer (Osirix by Pixmeo, Bernex, Switzerland). In one of the ischemic dogs (LAD stenosis), the SI-time curves for the real-time scan were generated by analyzing all diastolic frames and measuring the mean intensity inside 3 regions of interest (ROIs): LV bloodpool, normal myocardium, and hypoperfused myocardium. Similarly, SI-time curves were generated for corresponding ROIs in the gated FPP image series.

For each of the ischemic animal studies (n=4), a "representative" frame for the gated scan was selected from the images acquired during the myocardial enhancement phase that best visualized the perfusion defect. Next, a representative real-time frame was selected that best matched the corresponding representative gated frame in terms of (i) myocardial enhancement phase, and (ii) cardiac phase. The former was facilitated by counting the number of heart beats (in the reconstructed real-time series) from the start of LV enhancement and matching that to the gated image. Subsequently, for the selected R-R cycle in the real-time FPP image series (8 frames/s), one of the frames that best matched the gated image was selected.

The myocardium in all representative frames (one gated and one real-time for each ischemic study) were manually contoured by two readers to identify a contiguous perfusion defect (hypointense region) in the LAD territory as hypoperfused region, and to select a normal/remote region (similar regions between the real-time and gated frames). This was followed by quantitative analysis of: (i) the mean myocardial SI in the ischemic and normal regions for the real-time images; (ii) measurement of the defect area (in mm$^2$ units). To compare the contrast properties of the real-time and gated FPP images, the difference between mean SI in the normal and hypoperfused regions of the representative frame was computed for all FPP image series. This quantity was then divided by the estimated noise standard deviation (computed as the standard deviation of the SI in the normal myocardial region). The result is the pCNR defined above. The measurements by the two readers were averaged and used for the SI, contrast, and defect area comparisons.

Results

Figure 7:
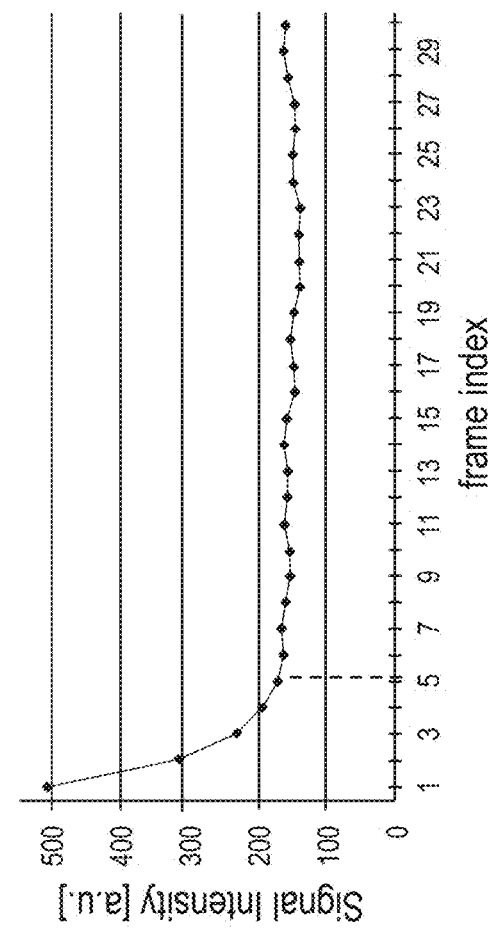
FIG. 7 demonstrates, in accordance with an embodiment of the invention, verification of fast transition to approximate steady state for the imaged slice. (a) and (b) show the 1$^{st}$ and 5$^{th}$ reconstructed frames for one of the animal studies with coronary stenosis, corresponding to the 0 s and 0.5 s time points during the real-time scan, respectively. The windowing is kept the same for the two frames and the highlighted box shows a selected ROI adjacent to the heart. (c) Average signal intensity (SI) in the ROI for the first 30 frames (not scaled, arbitrary units). The fast transition to steady state can be seen by comparing (a) and (b) and also by observing the SI behavior in (c). The mean SI in the ROI for the 5$^{th}$ frame shown in (b) is only 15% higher than the estimated steady state value (estimated as the mean ROI intensity averaged over the last 10 frames).
Figure 7:
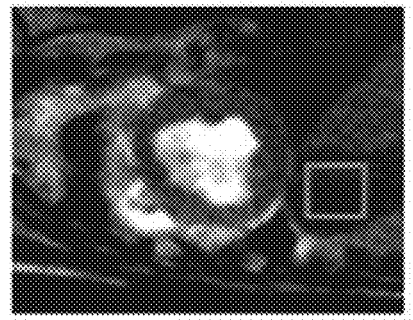
Figure 7:
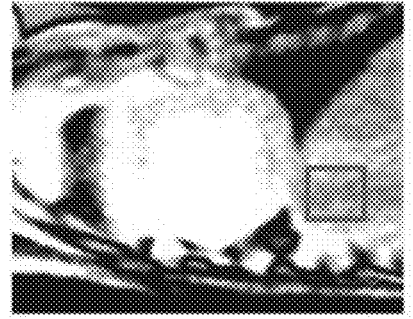

To verify the fast transition to T1-weighted contrast (approximate steady state) for the imaged slice, FIGS. 7(a)-(b) show the $1^{st}$ and $5^{th}$ reconstructed frames for one of the animal studies with coronary stenosis, corresponding to the 0 s and 0.5 s time points during the real-time scan, respectively. The windowing is kept the same for the two frames and the highlighted box shows a selected ROI adjacent to the heart. FIG. 7(c) depicts the mean intensity in the ROI for the first 30 frames (one frame every 125 ms). Comparing (a) and (b) or observing the signal behavior in (c) demonstrates the fast transition to steady state. Specifically, the mean intensity for ROI in $5^{th}$ frame shown in panel (b) is only 15% higher than the steady state value (average of the last 10 frames).

Figure 8:
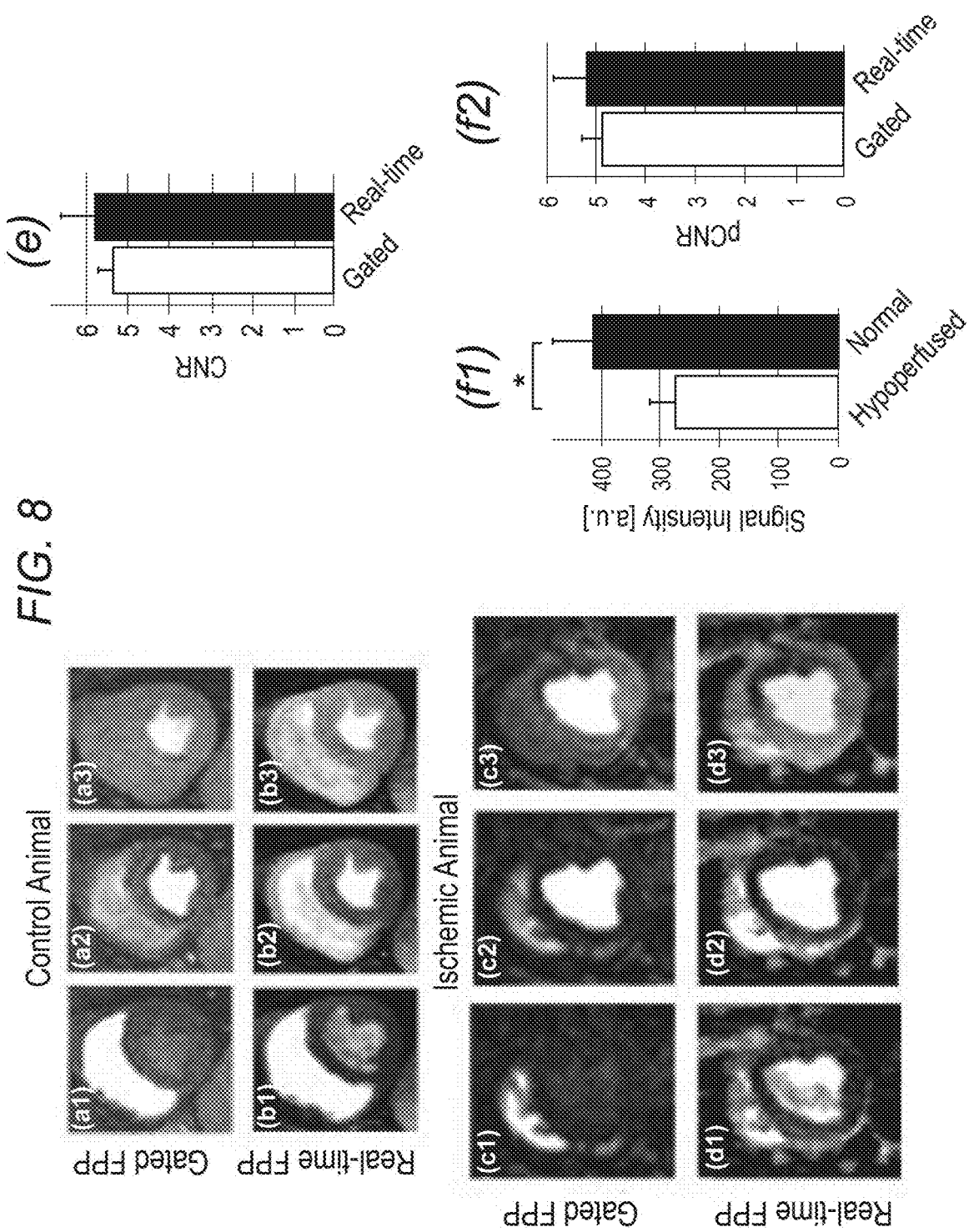
FIG. 8 demonstrates, in accordance with an embodiment of the invention, first-pass perfusion images from the control study and one of the ischemic (LAD stenosis) animal studies. The real-time frames were selected to closely match the cardiac phase and contrast enhancement phase of the corresponding gated (conventional) FPP images. The 1$^{st}$, 2$^{nd}$, and 3$^{rd}$ columns show example images from the RV, LV, and myocardial enhancement phases in the FPP series, respectively: (a1)-(a3): gated scan, control dog, heart rate (HR): 58 bpm; (b1)-(b3): real-time scan, control dog, HR: 57 bpm; (c1)-(c3) gated scan, ischemic dog, HR: 95 bpm; (d1)-(d3) real-time scan, ischemic dog, HR: 98 bpm. The in-plane spatial resolution for the real-time and gated images are 1.7×1.7 mm$^2$ and 2.4×1.8 mm$^2$, respectively. Windowing is the same for each row but varies row to row. The real-time frames are artifact-free and the perfusion defect area in (c3) closely matches the one in (d3). (e) Comparison of image quality in terms of contrast-to-noise ratio (CNR) across all animal studies (n=5) where CNR is defined as the myocardial contrast difference between the peak enhancement phase and the pre-contrast phase (real-time: 5.82±0.92 vs. gated 5.36±0.36; p=0.34). (f1,f2): Summary of the image contrast analysis for the ischemic dog studies (n=4) comparing the proposed real-time FPP method and the gated (conventional) method; (f1): Average myocardial signal intensity in the hypoperfused (ischemic) and normal (remote) regions for the representative real-time FPP images (normal: 410±69 vs. hypoperfused: 276±42; p<0.005); (f2): Hypoperfused-to-normal CNR (pCNR) for the real-time FPP images versus the gated FPP images. Overall, the real-time FPP images have a similar pCNR compared to the gated images (real-time: 5.18±0.70 vs. gated: 4.88±0.43; p=0.32).

In FIG. 8, example FPP images for the gated and real-time methods are shown: rows (a)-(b) correspond to the control study (dog with no stenosis) and rows (c)-(d) correspond to one of the ischemic (LAD stenosis) studies. The $1^{st}$, $2^{nd}$, and $3^{rd}$ columns show example images from the right ventricular (RV), LV, and myocardial enhancement phases in the FPP image series, respectively. The frames for the real-time method were selected so that they closely match the cardiac phase and contrast enhancement phase of the corresponding gated FPP images. The windowing (gray scale) is kept the same for each row (varies from row to row). The in-plane spatial resolution for the real-time and gated images are 1.7×1.7 mm$^2$ and 2.4×1.8 mm$^2$, respectively. The average HR for the scans corresponding to rows (c) and (d) were 95 bpm and 98 bpm, respectively. The real-time frames are artifact-free (no streaking or dark-rim) and the myocardial enhancement is clearly seen by comparing the $2^{nd}$ and $3^{rd}$ rows. Also, the perfusion defect area in (c3) closely matches the one in (d3). FIG. 8(e) compares the image quality of real-time and gated FPP images in terms of CNR (see above for definition), showing a similar performance (real-time: 5.82±0.92 vs. gated: 5.36±0.36; p=0.34). Note that the reported CNR values are not adjusted for the higher resolution/bandwidth of the real-time method compared to the gated method. Specifically, to adjust for spatial resolution differences, the CNR values for the real-time method should be multiplied by ≈1.5.

The inventors compared the perfusion defect area (in mm$^2$ units), measured from the two sets of FPP images (real-time vs. gated) across all animals (n=5), and least-squares regression showed a strong agreement (slope=1.05; intercept=−9.7 mm$^2$, R$^2$=0.98). A summary of the image contrast analysis for the ischemic dog studies (n=4) are presented in FIG. 8 (f1,f2). The myocardial SI for the real-time FPP images (average value of the hypoperfused region vs. normal region in the representative frames) are compared in panel (f1). The results show a marked SI difference, which enables delineation of the normal and hypoperfused regions for the real-time FPP images (normal: 410±69 vs. hypoperfused: 276±42; p<0.005). The result of the hypoperfused-to-normal myocardial CNR (pCNR) comparison between the real-time and gated FPP images is described in panel (f2). Overall, the real-time FPP technique has a similar pCNR compared to the gated method (real-time: 5.18±0.70 vs. gated: 4.88±0.43; p=0.32).

Figure 9:
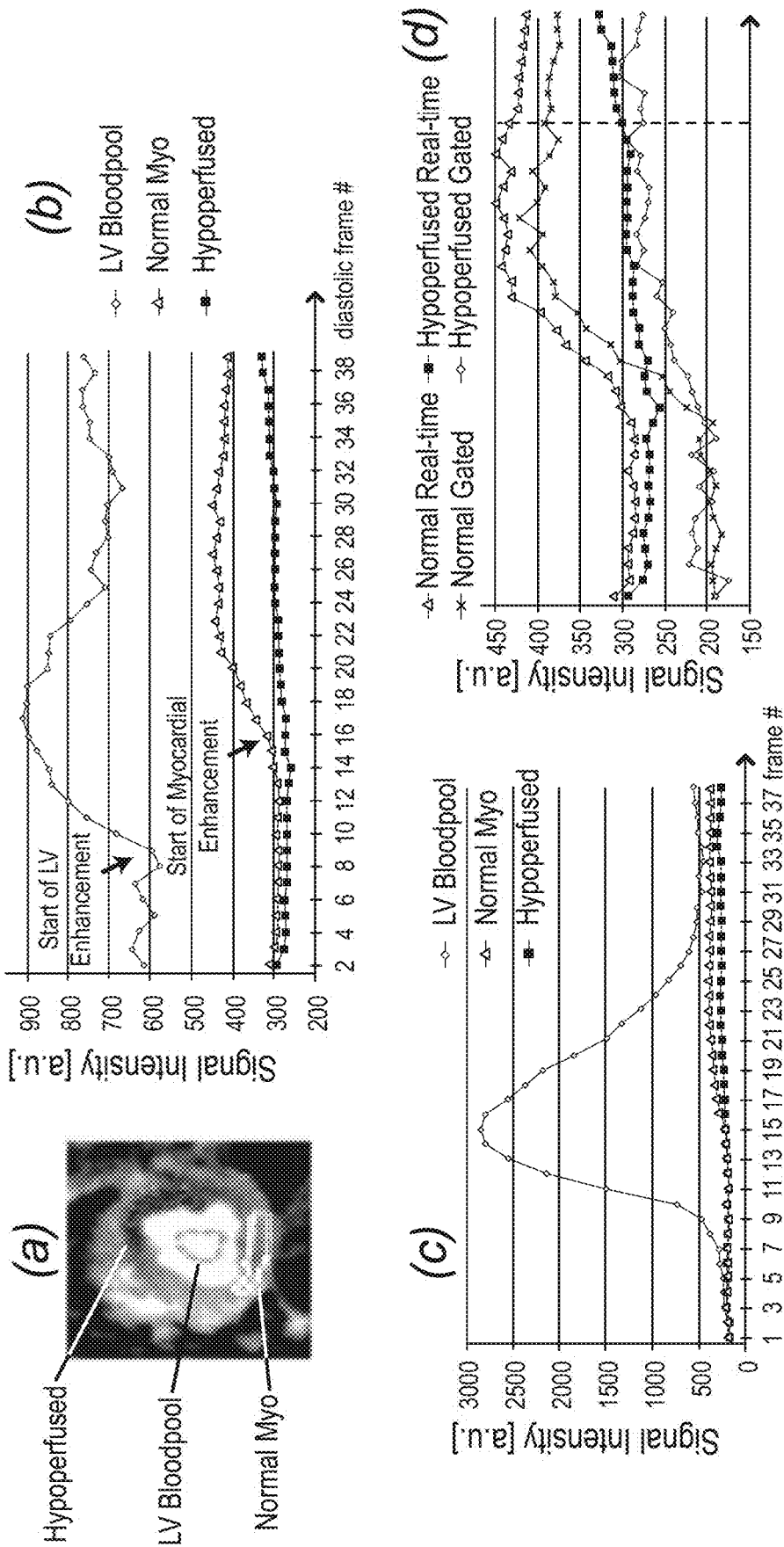
FIG. 9 demonstrates, in accordance with an embodiment of the invention, (a,b) Example SI-time curves for the proposed real-time FPP method: (a) selected ROIs in the LV bloodpool, remote region (normal perfusion), and ischemic region (hypoperfusion) for one of the ischemic animals (same as FIG. 8): (b) mean SI in each region (arbitrary units, same scale for all plots as a function of time (38 cardiac cycles are shown; average HR: 98 bpm). Arrows in (b) point to start of LV bloodpool and myocardial enhancement. (c) SI-time curves for the corresponding gated scan (average HR: 95 bpm). (d) Myocardial SI-time curves from (b) and (c) overlaid with no rescaling. The dotted line in (d) highlights the myocardial enhancement phase (Panels (c3) and (d3) in FIG. 8), and demonstrates the similar SI difference (contrast) between the normal and hypoperfused curves. The myocardial SI-time curves for the real-time method show a slower contrast uptake for the ischemic region compared to the remote region, which is consistent with the gated scan. However, the bloodpool SI for the real-time method exhibits significantly higher saturation effects compared to the gated method.

FIG. 9 shows the contrast dynamics for the real-time FPP method in one of the ischemic animals (same dog as panels (c)-(d) of FIG. 8) and compares the SI-time curves to that of the gated scan. Panel (a) defines 3 ROIs in: LV bloodpool region, remote myocardial region (normal perfusion), and ischemic region (hyperperfused), respectively. Panel (b) depicts the mean SI in each region (same scale for all plots) for 38 cardiac cycles ($2^{nd}$ to $39^{th}$ heart beats; average HR: 98 bpm). The two arrows in Panel (b) point to start of LV bloodpool enhancement (arrival of contrast in the LV cavity) and start of myocardial enhancement. Panel (c) shows the SI-time curves for the corresponding gated scan (average HR: 95 bpm). To better compare the temporal behavior of the myocardial SIs between the real-time and gated methods, the myocardial SI-time curves from the gated and real-time scans in (b) and (c) are displayed together in panel (d) (no normalization or scaling). The dotted line in (d) highlights the myocardial enhancement phase (panels (c3) and (d3) in FIG. 8), and demonstrates the similar SI difference (contrast) between the normal and hypoperfused curves. Overall, the results demonstrate that the SI-time curves for the real-time FPP images show a slower contrast uptake (lower upslope) for the ischemic region compared to the remote region, which is consistent with the myocardial SI-time curves for the gated scan.

Discussion

The need for ECG gating for first-pass perfusion (FPP) myocardial imaging protocols imposes practical difficulties and potentially reduces the diagnostic performance in patients undergoing cardiac exam for the assessment of coronary artery disease (CAD). An accurate, ungated, FPP technique may help widen the overall adoption of FPP cardiac MRI. As demonstrated herein, the inventors studied the feasibility and effectiveness of real-time FPP imaging using an optimized, ungated, high-resolution T1-weighted acquisition employing continuous radial sampling with a golden-angle trajectory. The T1-weighting and contrast properties of the sequence are magnetization driven, i.e., are provided by the approximate steady-state magnetization. In-vivo results show that the real-time method described in this section is capable of generating high-resolution FPP images (1.7×1.7×6 mm$^3$) in the setting of acute ischemia, while matching the conventional technique in terms of the hypoperfused-to-normal myocardial CNR. Furthermore, the experimental studies in animals show that the perfusion defect areas detected by the real-time method are consistent with the conventional technique.

The in vivo results presented in this work are the first demonstration—in the setting of myocardial ischemia—of the effectiveness of a real-time FPP method with ungated magnetization-driven acquisition (i.e., without SR or IR magnetization preparation). The high HRs for the ischemic animals (average: 92 bpm) indicate that the method can be effective for stress imaging wherein such high HRs are typically observed. In fact, the high frame-rate combined with properties of golden-angle radial sampling enables the method to produce at least one frame per R-R interval even at high HRs, and potentially under severe arrhythmia. However, the current method is limited to imaging a single slice during a breathhold using a simple apodized regridding reconstruction with no temporal acceleration or parallel imaging. One of skill in the art would readily appreciate that extension to accelerated multi-slice or volumetric acquisition (e.g., employing 3D parallel imaging) is also contemplated by the inventors.

The inventors' results show that the real-time method described in this section yields high-resolution images (1.7× 1.7 mm$^2$ in-plane) and, relative to the gated method, the perfusion defect can be clearly visualized with good CNR and no dark-rim artifacts (FIG. 8). As demonstrated in FIG. 9, the overall temporal behavior of the signal intensities for the real-time FPP method is similar to the conventional gated method. However, comparing FIGS. 9(b) and 9(c), the signal saturation effects in the LV bloodpool (nonlinearity between the contrast concentration and image intensity) is significantly higher for the real-time method compared to the conventional method. In the context of magnetization-driven acquisition, this is due to the low flip angle used, which is optimized for CNR to maximize the sensitivity of the FPP method, but is quite suboptimal in terms of linearity. Consequently, estimation of an arterial input function and quantitative blood flow assessment can be challenging.

One factor that disturbs the steady-state in real-time FPP acquisition is T1 changes due to wash in/out of contrast, which generally affects dynamic contrast enhanced MRI. However, the inventors did not observe significant pCNR variation between consecutive diastolic frames during the myocardial enhancement phase, as, for example, seen in FIG. 9(d). While not wishing to be bound by any one particular theory, this implies that such T1 changes are slow relative to the speed of steady-state transition (from perturbed steady-state back to approximate steady-state). Another process that perturbs the magnetization steady-state is cardiac motion (through-plane motion and in-flow effects during each cardiac cycle), which may result in small but noticeable signal intensity modulations due to changes in T1 sensitivity. It should be mentioned that an alternative to GRE-based steady-state acquisition for FPP imaging is SSFP imaging (as described in Giri et al. Steady-state first-pass perfusion (SSFPP): A new approach to 3D first-pass myocardial perfusion imaging. To appear in Magn. Reson. Med. 2013. doi: 10.1002/mrm.24638., which is incorporated by reference herein in its entirety), which achieves higher SNR and contrast.

Conclusion

The presented methods and results of this section establish that real-time MRI using ungated magnetization-driven acquisition with continuous radial sampling is an excellent method for myocardial perfusion imaging.

Example 4

Experiments IV

Background

As indicated above, first-pass perfusion (FPP) cardiac MR (CMR) imaging has been shown to have a high performance for diagnosis of coronary artery disease (CAD). Reliability of FPP imaging, however, is hindered by dark-rim artifacts (DRAs) and the need for near-perfect ECG gating. As indicated above, the latter can be challenging in the presence of arrhythmias or heart-rate variations during stress. Moreover, end systolic (ES) imaging has recently been shown to provide improved visualization of subendocardial defects. The inventors developed an innovative ungated FPP technique capable of simultaneously eliminating DRAs and enabling reconstruction of all slices at ES. The developed method achieves DRA-free imaging and high accuracy in patients with suspected CAD, using nuclear myocardial perfusion imaging (MPI) as the reference.

Methods

Figure 11:
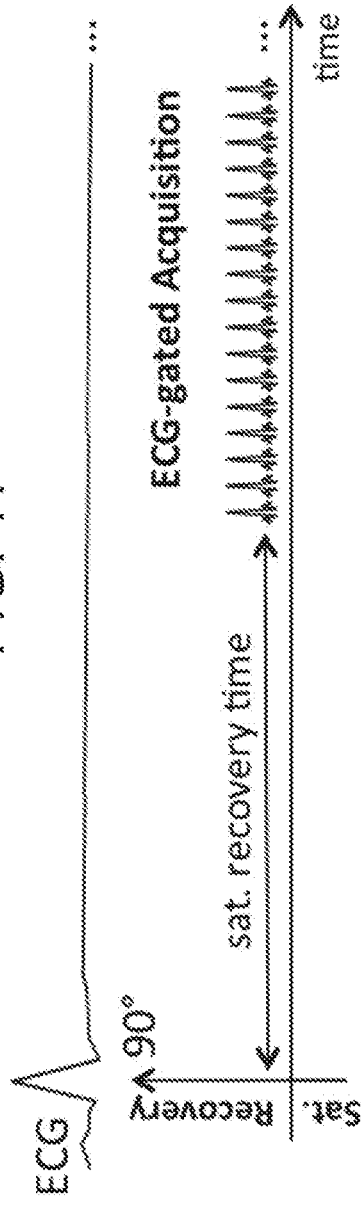
FIG. 11 depicts, in accordance with an embodiment of the invention, (a) a schematic for a conventional first-pass perfusion (FPP) pulse sequence with saturation recovery (SR) preparation and ECG synchronization. (b) A schematic for an inventive ungated Cine FPP pulse sequence using non-ECG-gated continuous golden-angle radial acquisition that is interleaved between 3 short-axis slices.
Figure 11:
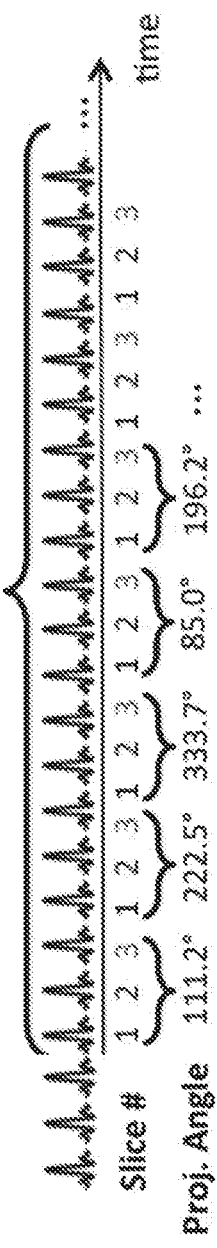

Based on the so-called "Ungated Cine FPP" approach, a multi-slice magnetization-driven method was developed for ungated FPP imaging. FIG. 11 highlights the main differences of the pulse sequence for this experiment compared with the conventional FPP method. All scans were performed on a 3T clinical scanner using an ungated RF-spoiled GRE sequence with continuous golden-angle radial acquisition as in FIG. 11b (flip angle=21°, resolution: 1.7×1.7×10 mm). The reconstruction method used automatic self-gating and optimally apodized compressed sensing for DRA-free accelerated reconstruction. Normal subjects (n=6) were studied using both the inventive and conventional methods. Patients (n=9) with suspected CAD on the basis of recent abnormal SPECT/PET MPI underwent adenosine stress/rest FFP CMR. Three patients returned for a second study using the conventional method.

Results

Figure 12:
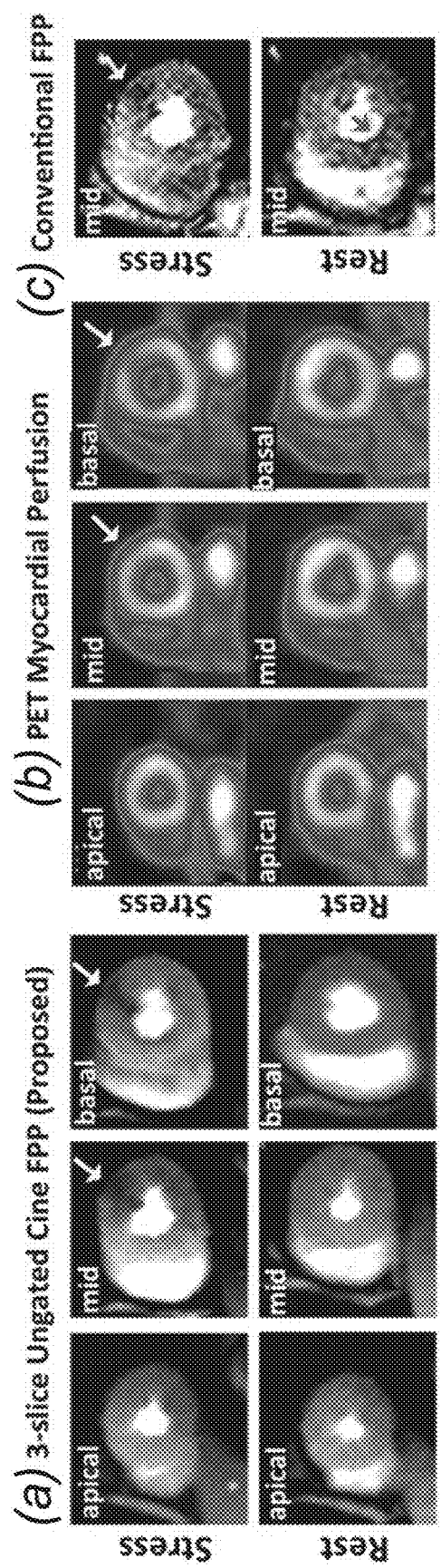
FIG. 12 depicts, in accordance with an embodiment of the invention, representative images from the CAD patient study (top row: vasodilator stress; bottom row: rest, arrows point to perfusion defects). (a) End-systolic 3-slice images for the ungated Cine FPP method (1.7×1.7 mm$^2$ in-plane resolution). (b) Corresponding PET myocardial perfusion slices (mild ischemia with 6% stress-induced defect in the anter-lateral wall at mild-basal slices). (c) Conventional ECG-gated SR-prepared FPP images (arrow in lower image points to dark-rim artifact). The ungated Cine FPP images are in strong agreement with the PET study and have higher quality than conventional FPP.

The ungated FPP studies in normal subjects were all of high quality and demonstrated normal perfusion. A representative patient study is shown in FIG. 12. Stress induced hypoperfusion was observed in the ES Ungated Cine FPP images, corresponding to a reversible defect on PET MPI (FIG. 12b). FIG. 12c shows the mid slice for the conventional FPP scan. Based on nuclear MPI studies, sensitivity and specificity of the developed method were 93% and 95%, respectively. The minor disagreements can be explained by the presence of subendocardial defects and possible artifacts on SPECT. All images were reviewed and no DRAs were detected on the Ungated Cine FPP images (2 readers, consensus). However, for the 3 studies using the conventional method, mild-moderate DRA was observed in 21% of the segments.

Conclusions

Conventional FPP methods are prone to DRAs, require accurate ECG gating, and do not provide the freedom to image all slices at ES. The developed method overcomes these challenges and is an attractive alternative with the advantage of simplicity (no gating), higher accuracy in the subendocardium (no DRAs, ES imaging), and thereby improved reliability. Results in healthy volunteers and patients with suspected CAD were of high quality and showed high accuracy compared to nuclear MPI.

Example 5

Experiments V

Summary

As indicated above, subendocardial dark-rim artifacts (DRAs) remain a major concern in first-pass perfusion (FPP) myocardial MRI and may lower the diagnostic accuracy for detection of ischemia. A major source of DRAs is the "Gibbs ringing" effect. As demonstrated herein, the inventors have developed an optimized radial acquisition strategy aimed at eliminating ringing-induced DRAs in FPP. By studying the underlying point spread function (PSF), it is shown that optimized radial sampling with a simple reconstruction method can eliminate the oscillations in the PSF that cause ringing artifacts. Realistic MRI phantom experiments and in vivo studies (n=12 healthy humans) were conducted to evaluate the artifact behavior of a new imaging scheme in comparison to a conventional Cartesian imaging protocol.

Simulations and phantom experiments verified the inventors' theoretical expectations. The in vivo studies showed that optimized radial imaging is capable of significantly reducing DRAs in the early myocardial enhancement phase (during which the ringing effect is most prominent and may obscure perfusion defects) while providing similar resolution and image quality compared with conventional Cartesian imaging.

The developed technical framework and results demonstrate that, in comparison to conventional Cartesian techniques, optimized radial imaging, with the optimizations described herein below in greater detail, significantly reduces the prevalence and spatial extent of DRAs in FPP imaging.

Introduction

Dark-rim artifacts (DRAs) are a major drawback for accuracy and widespread adoption of FPP imaging because they impede diagnosis of hypoperfusion in the subendocardium, which is the most and typically the earliest affected myocardial layer in ischemic disease. Specifically, when FPP is used to diagnose patients with mild or moderate levels of hypoperfusion, DRAs may be interpreted as perfusion defects and therefore may reduce the diagnostic specificity. Alternatively, they may reduce the sensitivity if the reader dismisses true deficits as artifacts. Another example highlighting the need for eliminating DRAs is the diagnosis of patients with coronary microvascular dysfunction, because their perfusion deficits tend to be mild and subendocardial. Therefore, establishing an acquisition scheme that is robust to DRAs can significantly increase the diagnostic performance of FPP imaging and its clinical use for a variety of patient cohorts.

For qualitative (visual) assessment of FPP, the current approaches for distinguishing artifacts from true deficits (e.g., examining the spatial/temporal characteristics of the artifact or stress-rest comparisons) are subjective and, though potentially helpful, do not provide a systematic solution and are limited due to inherent variability of DRAs. Furthermore, even if an experienced reader can "read through" DRAs, it could be the case that some subendocardial deficits "fill in" early while the DRA is still present—that is, during the early myocardial enhancement phase. This will inevitably result in missed or misread perfusion defects. Moreover, in quantitative perfusion assessment, the DRA problem is even worse and may result in significant errors. DRAs have been linked to multiple factors, including: Gibbs ringing or truncation artifact, cardiac motion, susceptibility effects from contrast dynamics, and signal variation during acquisition. Recently, there have been several attempts at minimizing DRAs, mainly by improving the spatial resolution using temporally accelerated reconstruction—for example, using model-based (so called "k-t") or compressed sensing techniques. Attempts at decreasing DRAs based on increased spatial resolution are motivated by minimizing the "Gibbs ringing" effect that is thought to be a central source of DRAs. Gibbs ringing is a fundamental property of practical Fourier imaging systems, because the underlying spectrum (k-space data) has infinite support but is approximated by a finite number of samples. The ringing phenomenon refers to oscillations in the reconstructed image intensity that include signal dips (undershoot) at sharp image edges (e.g., the left ventricle (LV) cavity—endocardium boundary), which may manifest as the DRA. In the experiments reported in this section of the application, the focus is on the contribution of Gibbs ringing to DRAs, and a radial imaging strategy that effectively eliminates ringing-induced artifacts is demonstrated.

The first objective was to design and optimize a radial sampling scheme that, combined with a simple reconstruction scheme, is virtually free of ringing-induced artifacts. Based on theoretical derivations combined with numerical and imaging verifications, it was determined that optimized radial imaging with wide k-space coverage can effectively remove Gibbs ringing effects. The second objective of the work reported in this section was to evaluate whether radial imaging using the optimized scheme would significantly reduce the prevalence and spatial extent of DRAs in FPP imaging compared with the conventional Cartesian technique, while providing equivalent resolution and similar image quality.

Theory

Preliminaries

The following terminology and notations are used in connection with Cartesian and radial sampling schemes. The number of readouts is denoted by $N_{RO}$ and the number of samples per readout by $N_S$. The field of view (FOV) along the "readout direction" (x or r for Cartesian and radial sampling, respectively) is assumed to be the interval $[-L;L]$ for a fixed $L>0$. Therefore, the readout resolution (for either scheme) is proportional to $N_S$. In Cartesian and radial k-space, the readout dimension is denoted by $k_x$ and $k_r$, respectively, and the sampling interval along readout $\Delta k$ is assumed to satisfy the conventional two-fold oversampling (relative to the Nyquist criterion) used in modern MR scanners—namely, $\Delta k < 1/4L$: For Cartesian sampling, the inventors refer to "readouts" to denote the phase-encoding (PE) lines, "readout resolution" to represent the resolution along the frequency encode (FE) direction, and "samples per readout" to be the number of FE samples. In general, the spatial resolution along a certain dimension is proportional to the maximum sampled frequency along the corresponding k-space dimension, denoted by adding a superscript max to the k-space dimension. Specifically, $k_y^{max}=N_{RO}\Delta k/2$ determines the PE resolution, and the readout resolution for Cartesian and radial sampling are determined by $k_x^{max}=N_S\Delta k/2$ and $k_r^{max}=N_S\Delta k/2$; respectively. Finally, the inventors assume uniform sampling between the readouts—that is, uniform PE spacing ($1/FOV_y$) for the Cartesian scheme and uniform angular sampling for the radial scheme.

Point Spread Function Analysis: Sufficiently Sampled (Ideal) Scenario

The differences in the general properties of Cartesian and radial k-space sampling schemes were studied, focusing on the components that contribute to ringing artifacts in the acquired images. A classical method for describing the effect of different sampling patterns in imaging is to characterize the corresponding point spread function (PSF). Given the PSF corresponding to a k-space sampling pattern, the reconstructed image is the result of two-dimensional (2D) convolution of the PSF with the magnetization density (i.e., the ground-truth image). FIG. 13a depicts an example of isotropic-resolution Cartesian and radial sampling patterns with the same resolution $k_x^{max}=k_y^{max}=k_r^{max}$.

To study the Cartesian acquisition scheme, the inventors calculated the PSF for a Nyquist-sampled Cartesian pattern with $N_{RO}$ readouts (PEs) and Ns samples per readout (FEs). Without loss of generality, it is assumed $N_{RO}=256$ and Ns=192. The FOV along y is assumed to be 25% smaller, yielding a rectangular FOV, which is typically used in Cartesian imaging. The PSF is numerically approximated by 20-fold zero-padding of an all unity k-space matrix of 256×192 (equivalent to the underlying image being a 2D Dirac delta function) and computing the 2D inverse discrete Fourier transform. The resulting real-valued image is then scaled (peak value normalized to 1) to yield the PSF in (x,y) domain. FIG. 13b1 shows the absolute value of the computed 2D PSF for the described Cartesian scheme (two-fold zoom). The analytical PSF expression for 2D Cartesian sampling is the well-known 2D periodic sinc function, which is also called the Dirichlet kernel:

$$PSFc(x, y) = \Delta k^2 \frac{\sin(2\pi x k_x^{max})}{\sin(\pi x \Delta k)} \frac{\sin(2\pi y k_y^{max})}{\sin(\pi y \Delta k)} \quad [1]$$

FIG. 13b2 shows a one-dimensional (1D) cut of the PSF along the y, which coincides with the x-axis cut (consistent with Eq. [1] of this section). If convolved with a 2D image with sharp edges (e.g., blood pool-myocardium border in FPP images), these oscillations will result in image artifacts, referred to as Gibbs ringing artifacts. In effect, signal values around the image edge are modulated by the positive/negative side-lobes of the PSF, resulting in reconstructed intensities above/below the ground truth.

Next, the PSF was computed for a radial acquisition scheme with the same readout resolution (Ns=256) and $N_{RO}$=402 readouts (projections), which matches the requirement for zero angular aliasing according to the Nyquist criterion. The radial PSF is computed as follows: (1) sampling a uniform (all unity) k-space along the described radial trajectory; (2) regridding the sampled data using a conventional Kaiser-Bessel gridding kernel (width 4) and density compensation function (DCF); and (3) scaling the resulting real-valued image (peak normalized to 1). This conventional DCF is ramp-shaped and equal to $|k_r|$ (except for the origin), which hereafter is referred to as the "ramp DCF." The corresponding PSF (absolute value) is shown in FIG. 13c1. The analytical formula describing the behavior of this circularly symmetric PSF in (r,θ) polar coordinates can be written as:

$$PSF_R(r) \approx \frac{\pi(\Delta k)^2}{4} + (2k_r^{max})^2 \, jinc(2k_r^{max} r) \qquad [2]$$

where $jinc(r)=J_1(\pi r)/2r$, in which $J_1(r)$ is the first-order Bessel function. This radially symmetric function has been described before in the MR literature by Lauzon and Rutt using classical results from radio astronomy.

The jinc function in Eq. [2] of this section is the analog of sinc (Eq. [1] of this section) in 2D polar coordinates and is equal to the spectrum (Hankel transform) of a unit-height disk. Note that the PSF depicted in FIG. 13c1 does not exactly conform to Eq. [2] of this section because of the effects of higher order terms in the PSF located at multiples of $1/\Delta k$ in addition to underlying numerical errors. However, these effects are negligible for the described sampling scheme, and FIG. 13c1 closely follows $|PSF_R(r)|$ because the effect of higher order terms is negligible for a small enough readout sampling interval $\Delta k$, satisfying $\Delta k<\frac{1}{4}L$. Specifically, this condition ensures that the "polar ring" components of the radial PSF can be ignored in the imaged FOV. FIG. 13c2 shows a 1D cut of the real-valued PSF along y. Similarly to Cartesian imaging, the PSF consists of a narrow main lobe and oscillating side lobes, which may also result in ringing artifacts when convolved with the underlying image; this effect is sometimes referred to as "radial ringing" in MRI literature or as the "Airy pattern" in Fourier optics.

Figure 13:
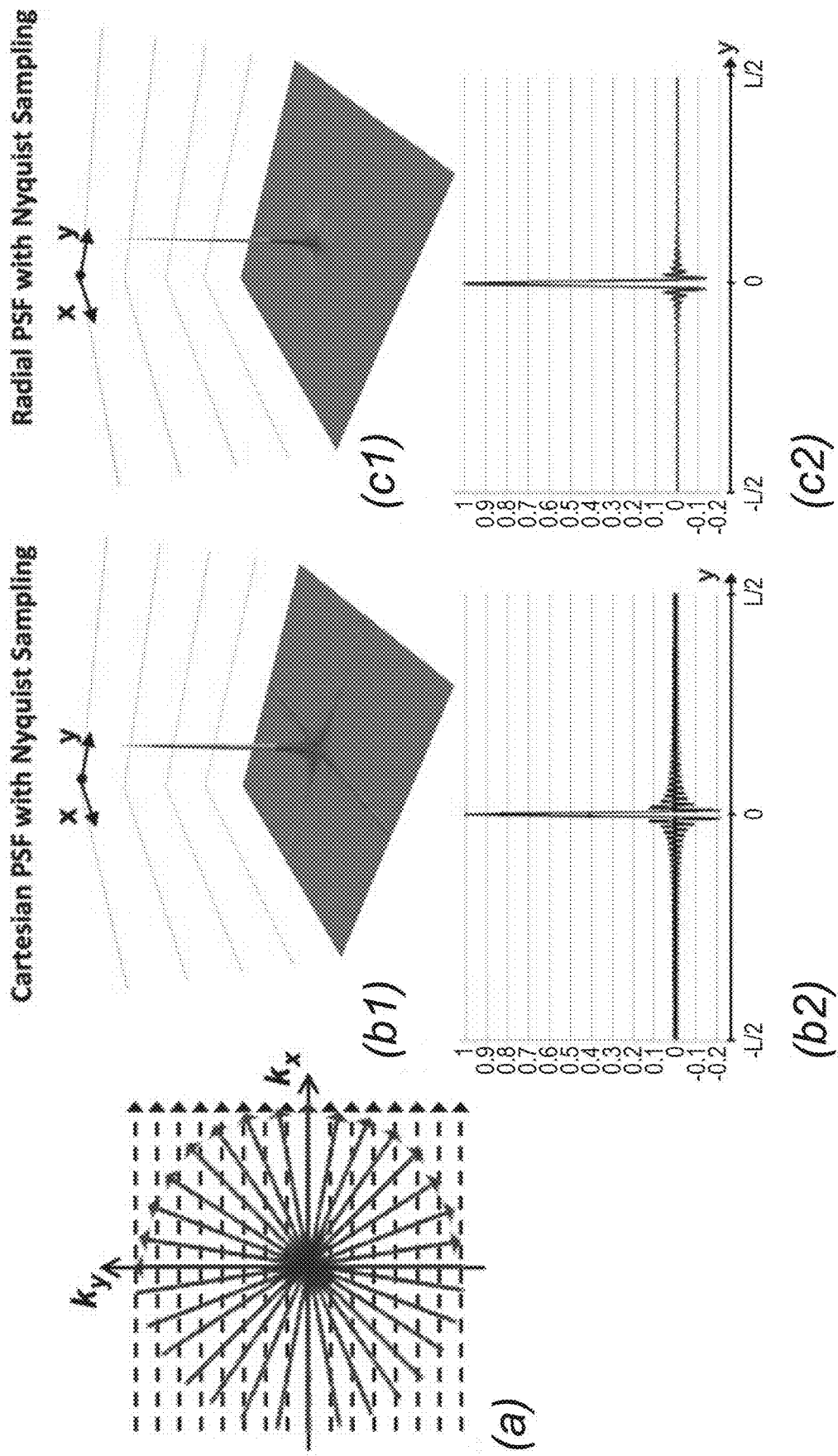
FIG. 13 depicts, in accordance with an embodiment of the invention, PSF analysis for the sufficiently sampled scenario. a: Schematic for sufficiently sampled Cartesian and radial sampling patterns with the same readout resolution. b1, c1: Absolute value of the PSFs for Nyquist-sampled Cartesian and radial acquisitions, respectively with $N_S$=256 samples per readout and a fixed FOV of [−L,L]). b2, c2: 1D cuts of the respective PSFs along the y axis (same as the cut along x axis).

For both Cartesian and radial schemes, the frequency (spatial density) of PSF oscillations is proportional to the resolution (FIGS. 13b2 and 13c2). Consequently, any potential ringing-induced DRAs become more compact and therefore visually less significant. However, a key difference between Cartesian and radial schemes is that the oscillation frequency for radial PSF in both x and y directions only depends on the readout resolution, $k_r^{max}$ which is proportional to Ns. In contrast, the frequency of oscillations along y for the Cartesian PSF is a function of the PE resolution, $k_y^{max}$, which is proportional to $N_{RO}$. Therefore, increasing the oscillation frequency of the underlying PSF for radial imaging comes with almost no acquisition time penalty (since it only requires increasing Ns for a fixed FOV), whereas accomplishing the same for Cartesian imaging may incur significant acquisition time penalty, since it requires increasing $N_{RO}$ (i.e., more readouts). In addition to the oscillation frequencies, there are other differences between the characteristics of the PSFs shown in FIG. 13 (Eqs. 1 and 2 of this section), which include the peak amplitude and decay rate of the side lobes, both of which are more desirable for the radial PSF. However, these differences correspond to 1D cuts of the PSFs, and their effects on the reconstructed image are difficult to analyze analytically. Consequently, numerical simulations were used to study such differences (see the Methods of this section).

PSF Analysis: Limited Readouts (Practical) Scenario

Figure 14:
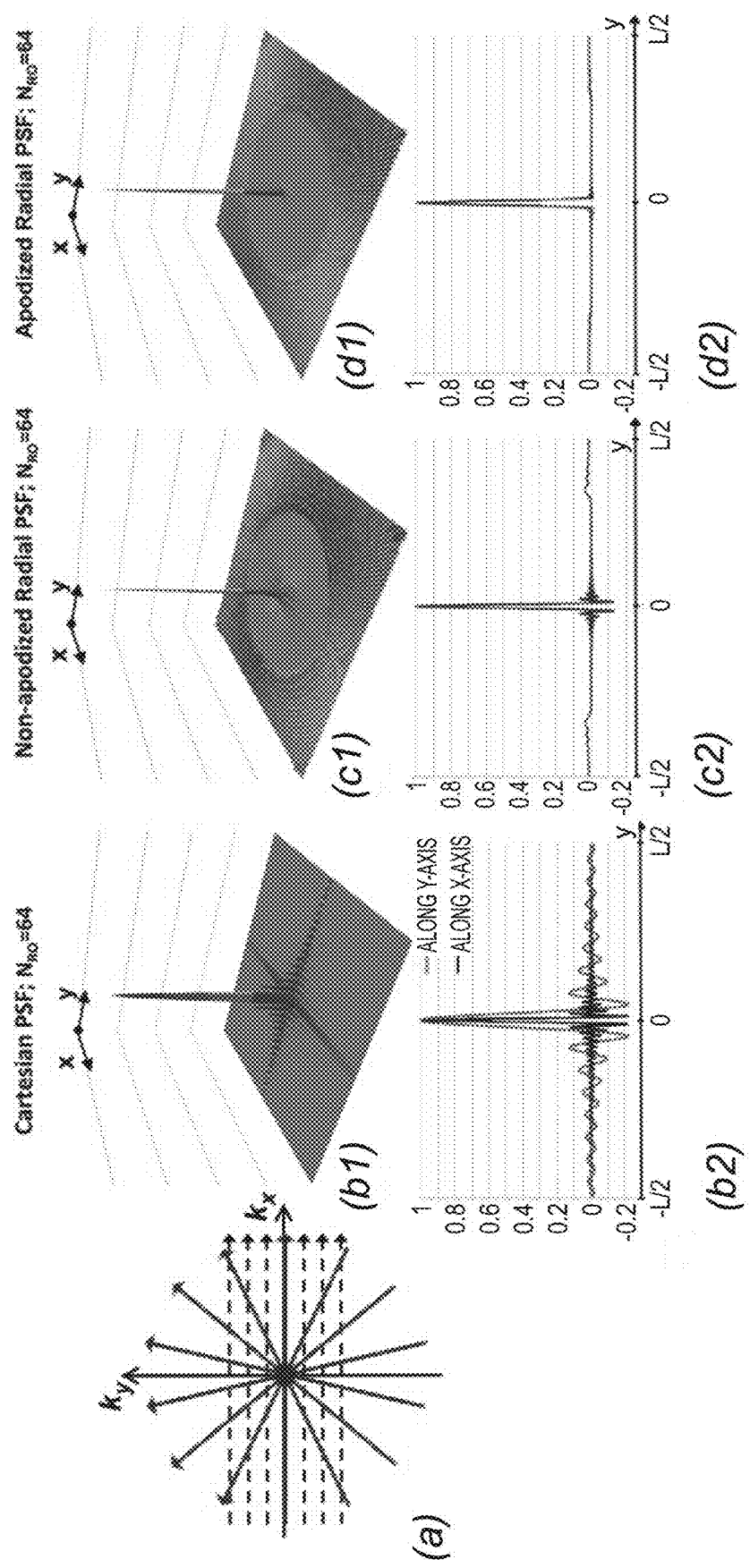
FIG. 14 depicts, in accordance with an embodiment of the invention, PSF analysis for the limited readouts scenario. a: Schematic for the limited readout sampling scenario for Cartesian and radial acquisition with equal number of readouts and readout resolution. b-d: PSFs with $N_{RO}$=64 readouts and $N_S$=256 samples per readout (fixed readout FOV [−L,L]). b1, b2: Absolute value of the Cartesian PSF and its 1D cuts along x and y; the FOV along the PE line is [−0.75 L, 0.75 L]. c1, c2 and d1, d2: Radial PSF and its 1D cut corresponding to nonapodized reconstruction and apodized reconstruction (apodizer as in Eq. [3] using Ω=1:17), respectively. In contrast to radial sampling, insufficient k-space coverage along ky (PE) in Cartesian sampling results in low-frequency oscillations along y (three-fold wider side lobes than x), as shown in panels b1 and b2.

FIG. 14 describes the PSF properties of Cartesian and radial acquisitions for a practical scenario wherein only a limited number of readouts is acquired, while the readout resolution is the same as before (Ns=256 samples). The schematic for this "limited readouts" scenario is depicted in FIG. 14a. In contrast to the previous section (the "sufficiently sampled" scenario in FIG. 13), here it is assumed that the same number of readouts $N_{RO}$ is acquired for both Cartesian and radial sampling schemes. Without loss of generality, in the following it is assumed $N_{RO}$=64. For Cartesian imaging, given the rectangular FOV (25% reduced FOV along PE), this sampling scheme implies a 3-to-1 resolution difference between x and y dimensions $k_y^{max}=k_x^{max}/3$. The corresponding PSF and 1D cuts are shown in FIGS. 14b1 and 14b2, respectively. The Cartesian PSF oscillations along y have a three-fold lower frequency compared with the one in FIG. 13b2 with similar peak side-lobe amplitudes. The wider main lobe along y implies lower spatial resolution; more importantly, the wider side lobes yield a wider (more spatially prominent) ringing artifact.

In the following, the inventors refer to conventional regridding reconstruction of radial acquisition using the ramp DCF as "nonapodized" reconstruction. The computed nonapodized radial PSF and its 1D cut are shown in FIGS. 14c1 and 14c2 and correspond to nonapodized regridding reconstruction of NRO=64 projections. FIG. 14c1 matches the previous description in the literature: the PSF for angularly undersampled radial acquisition consists of a superposition of the principal jinc component and its associated side lobes (FIGS. 13c1 and 13c2) plus the "streaking" components that start outside of a certain radius. This radius for the described sampling scheme is approximately 0:3 L, i.e., 15% of the FOV; also, the peak amplitude of the streaking components is located at 0:35 L and has a value of 3.4%. In comparison, the peak negative and positive side lobe amplitudes (jinc component) of this PSF are −13.2% and 6.4%, respectively, which is the same as the sufficiently sampled radial PSF in FIG. 13. The key observation in comparing the limited-readout radial scheme in FIGS. 14c1 and 14c2 with the sufficiently sampled one in FIGS. 13c1 and 13c2 is that both PSFs show almost identical oscillatory (jinc) components.

Comparing the radial and Cartesian sampling schemes in FIG. 14, it is worth emphasizing that the total acquisition time is the same between the two (note that $N_{RO}$=64 is fixed and that $k_x^{max}=k_r^{max}$). However, the radial trajectory samples the high-frequency k-space regions in all directions, yet the Cartesian trajectory misses some of the high frequency regions specifically along the PE direction, which results in low-frequency oscillations in the PSF along y. Hence, the expected ringing artifact for radial sampling (with nonapodized reconstruction) is expected to be less significant (i.e., narrower) compared with Cartesian sampling (along PE).

PSF Analysis: Radial Imaging with Optimized Apodization

The PSF for radial imaging also depends on the reconstruction method used, i.e., the PSF corresponding to nonapodized reconstruction (discussed above) is different from the one corresponding to filtered backprojection or regridding reconstruction incorporating apodization. Here, the radial PSF corresponding to regridding reconstruction using an apodized k-space weighting instead of the nonapodized ramp-shaped DCF was considered. The inventors used a Gaussian kernel as the "apodizer" (apodizing function) with the following form:

$$A(k_r) = \exp\left(-\pi\left(\frac{k_r/k_r^{max}}{\Omega}\right)^2\right) \quad [3]$$

for some pre-defined parameter $\Omega$. In the apodized reconstruction, the radial readouts are first multiplied by $A(k_r)$, which reduces the weighting of high-frequency k-space samples, before conventional density compensation (i.e., weighting by the ramp-shaped DCF) and regridding. The typical motivation for using an apodized reconstruction in projection imaging is to achieve high-frequency noise suppression to improve signal-to-noise ratio (SNR), which comes at the expense of reduced effective resolution. The equivalent image-domain operation for the described Gaussian apodization is smoothing by a 2D circularly symmetric Gaussian kernel. It can be shown that the effective full width at the half maximum of the underlying PSF will increase with decreasing $\Omega$, thereby reducing the effective isotropic resolution. Note that because $k_r^{max}$ is the same for the apodized scheme, the PSF oscillation frequency will stay the same, but the amplitude of oscillations can be significantly suppressed and even effectively eliminated for a small enough $\Omega$.

To apply the apodizer and study its effect of the radial PSF, it was necessary to choose an optimal parameter $\Omega$ for the Gaussian kernel in Eq. [3] of this section. The optimization criterion is to minimize the resolution penalty (reduction factor), i.e., to find the maximal $\Omega^*$ such that the peak negative side lobe of the resulting PSF will be lower than 1% (i.e., an apodizer that essentially eliminates all ringing components (side lobes) from the PSF). The Gaussian apodizer in Eq. [3] of this section can be shown to be near optimal in the sense of providing maximum suppression in the amplitude of the largest side lobe for a given resolution penalty. The proof is beyond the scope of this study, but a related work has been described recently for Fourier spectrometry (see Naylor D A, Tahc M L. Apodizing functions for Fourier transform spectroscopy. J Opt Soc Am A 2007; 24:3644-3648; which is incorporated herein by reference in its entirety). The result of the numerical search algorithm for the described radial sampling pattern was $\Omega^*=1.17$. To quantify the effect of the corresponding apodization on the reconstructed resolution, the FWHM of the main lobe of the resulting PSF was compared to that of the nonapodized PSF in FIG. 14c1. The ratio of FWHMs (apodized over nonapodized) is 1.28, implying a 1.28-fold reduction in effective resolution along x and y.

FIGS. 14d1 and 14d2 shows the radial PSF corresponding to the same sampling scheme as in FIGS. 14c1 and 14c2 but using the optimized apodized reconstruction instead of the nonapodized reconstruction. As seen in the 1D cut shown in FIG. 14d2, almost all ringing components were eliminated (peak negative amplitude=−0.95%, 14 times smaller than FIG. 14c2) and the streaking components were significantly reduced (peak streak amplitude=1.3%, 2.6 times smaller than FIG. 14c2). Therefore, in addition to improving SNR, the apodized reconstruction reduces streaking and effectively eliminates oscillations in PSF (source of ringing artifacts) at the cost of reduced resolution. An acquisition scheme that samples the data at this reduced resolution and does not use apodization is more SNR-efficient (compared with the apodized scheme) but will not achieve the desired reduction of the ringing components. In practice (and as described in the Methods and Results of this section), given a desired spatial resolution for the reconstruction, this tradeoff (resolution versus ringing) can be flexibly adjusted using the described Gaussian apodizer.

Methods

Numerical Simulation

The PSF properties described in the above section were verified by simulating k-space sampling and reconstruction for a noise-free numerical phantom consisting of two overlapping inner/outer disks (FIG. 15, top row) with the following specifications: ratio of inner to outer disk radius=$R_{in}/R_{out}=\tfrac{2}{3}$ and signal intensity ratio between the two disks was 6:1, which represents a maximal ("worst case") contrast ratio along the subendocardial border for FPP.

The inventors used the same Cartesian and radial sampling patterns as in FIG. 14. To compute the k-space data samples accurately for a given sampling pattern, the inventors applied the following analytical expression for $D(k_r)$, the circularly symmetric 2D Fourier representation of the described phantom:

$$D(k_r) = 10\pi \cdot R_{in}^2 \frac{J_1(k_r R_{in})}{k_r R_{in}} + 2\pi \cdot R_{out}^2 \frac{J_1(k_r R_{out})}{k_r R_{out}} \quad [4]$$

Phantom Experiment

Figure 16:
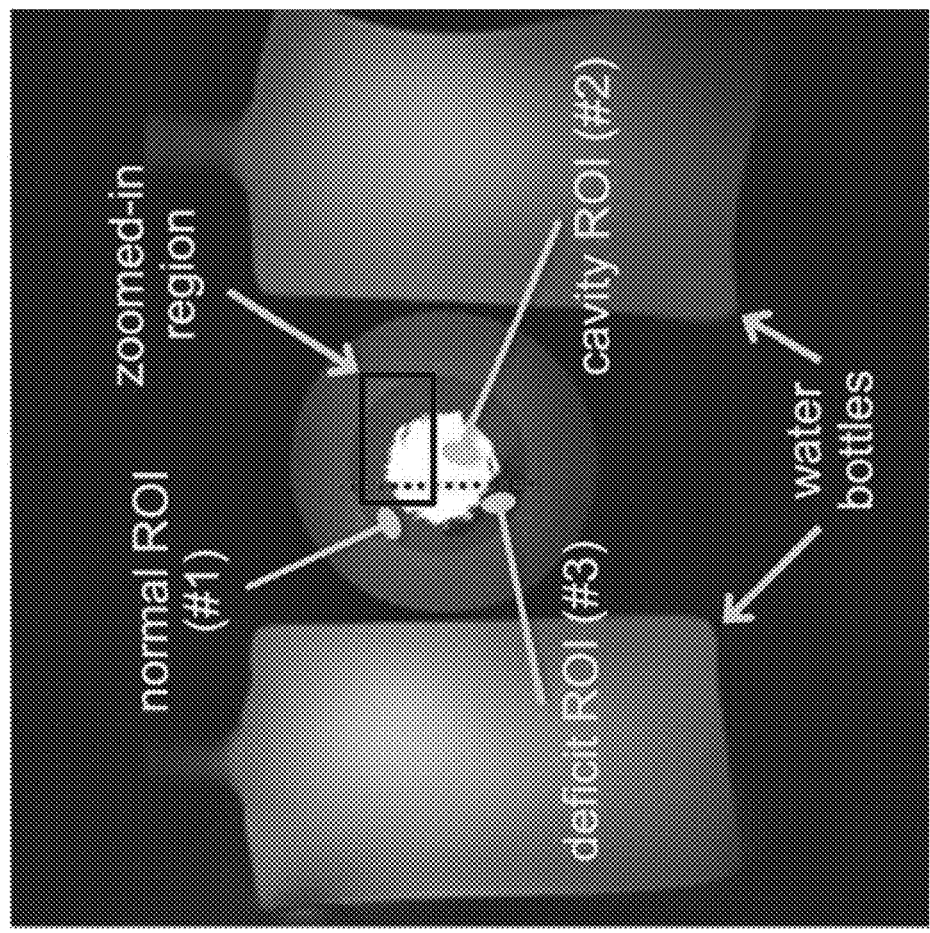
FIG. 16 depicts, in accordance with an embodiment of the invention, a description of imaged MR gelatin-Gadolinium phantom with realistic signal intensity ratios, used to demonstrate robustness of projection imaging to Gibbs ringing. The "ground truth" image is acquired at 1.0×1.0 mm$^2$ resolution using an SR-prepared FLASH radial pulse sequence with 384 readouts (projections). The ratio of the signal intensity in the cavity (ROI #2) to the normal region (ROI #1) is approximately 6:1 (range, 5.5-6.1). The cavity and normal regions were composed of a mixture of gelatin, saline, and contrast whereas the deficit region (ROI #3) contained almost no contrast agent. The T1 values ROI #1, #2, and #3, are approximately 750 ms, 60 ms, and 1200 ms, respectively (estimated based on pixel-by-pixel T1 fitting using Cartesian data acquired separately with six different inversion times). The highlighted box is the zoomed-in region shown in FIG. 17. The dotted line shows the location of the cut for the 1D profiles shown in FIG. 17.

To verify the theoretical assertions, an MR phantom intended to simulate a geometrically-realistic FPP scenario with worst-case signal intensity variations (similarly to the numerical phantom above) was designed. The phantom was composed of multiple regions of interest (ROIs) made of gelatin and saline doped with various concentrations of a Gadolinium-based contrast agent (gadoversetamide), and surrounded by two bottles. FIG. 16 shows the result of a fully sampled scan of the phantom, which was used as the "ground truth" image. The phantom was intended to resemble the left ventricle (ROIs: "LV cavity" region, "normal" region, "deficit" region) during the wash-in phase of the contrast agent, and the bottles were to represent the surrounding tissue. Further details including T1 values are included in the FIG. 16 description.

MR data was acquired on a 3T clinical scanner (Magnetom Verio; Siemens Healthcare, Erlangen, Germany) with a standard cardiac-torso receiver array. The scan parameters used to image the phantom in FIG. 16 (i.e., ground-truth scan) were as follows: radial FLASH with saturation recovery (SR) preparation; 1.0×1.0 mm² resolution; slice thickness: 6 mm; FOV: 384×384 mm²; 384 projections with 384 samples per readout; number of channels=15; receiver bandwidth=650 Hz/pixel; flip angle=12°; TR/TE=3.0/1.8 ms; and SR time=90 ms.

The ratio of the signal intensity in the cavity (ROI #2) to the normal region (ROI #1) was approximately 6:1 (range along the edge: 5.5-6.1). This signal intensity ratio is higher than the typical 5:1 or 3:1 ratio encountered in vivo. However, as stated above, the goal was to test the robustness of radial imaging (with wide k-space coverage) to ringing artifacts, and as such, the 6:1 ratio represents a worst-case scenario.

The inventors conducted Cartesian and radial phantom scans using Cartesian/radial SR-prepared FLASH pulse sequences. Both datasets were acquired using $N_{RO}$=77 readouts with Ns=256 samples per readout and similar sequence parameters as the ground truth scan above. Consequently, the acquired readout resolution for both datasets was 1.5 mm. The Cartesian scan used a rectangular FOV of 384×230 mm$^2$ (PE resolution: 3.0 mm). Two reconstructions were performed from the radial dataset: (1) nonapodized (k-space data only weighted by ramp DCF before regridding); and (2) Gaussian-apodized (data also weighted by the optimized Gaussian kernel before DCF weighting and regridding). All radial/Cartesian reconstructions used sum-of-squares coil combination followed by standard zero-filled interpolation to a 512×512 image matrix to minimize variability to sub-pixel shifts.

In Vivo Studies

Following informed consent, healthy human volunteers (n=12; 7 women, 5 men; average age=24 years) with no history of heart disease or diabetes were imaged on the same 3T scanner according to a study protocol approved by the Institutional Review Board at Cedars-Sinai Medical Center. Two FPP scans, both using SR-prepared FLASH acquisition, were performed at rest (breathhold scans during 50 heartbeats; mean scan time=42 s) using an optimized radial pulse sequence followed by the product FPP Cartesian sequence (see details below), with a 10- to 12-minute time gap between the two scans to allow for contrast washout. The contrast injection dose (gadoversetamide) for each perfusion scan was 0.04 mmol/kg. All scans were "single shot" (i.e., there was no data sharing between heartbeats), and the number of readouts was matched between the radial and Cartesian scans within ±3 readouts (range: 48-56). The readout resolution for the Cartesian scans was matched to that of the radial scan (range: 1.8-1.9 mm; average=1.8 mm; the reconstructed resolution for radial images was different, as described below, and the PE resolution was 2.7-2.9 mm (average=2.8 mm). The parameters for the Cartesian scan (product sequence) were as follows: FOV read=270-350 mm; flip angle=12°; 15 receiver channels; receiver bandwidth ≈680 Hz/pixel; TR=2.5-2.6 ms; TE=1.3-1.4 ms; SR time=100 ms with linear PE ordering; three contiguous slices per heartbeat (8 mm thickness, centered at midventricle), each acquired following a composite (product) SR preparation pulse train (see Kellman P, Arai A E. Imaging sequences for first pass perfusion—a review. J Cardiovasc Magn Reson 2007; 9:525-537; which is incorporated by reference in its entirety); TGRAPPA rate 2; online image reconstruction on the scanner. The radial FPP scans used a customized pulse sequence with similar parameters except the following: a fixed FOV of 285 mm (two-fold readout oversampling with 320 samples/spoke) and a BIR-4 adiabatic 90° pulse for SR preparation prior to acquisition of each slice. Due to the SAR limitations of the employed BIR-4 pulse at 3T, it was anticipated that the inventors would have been limited to acquisition of two slices per R-R interval for some of the subjects and therefore scanned one slice position (midventricular) two to three times per heartbeat in all radial scans. The motivation for using a BIR-4 SR pulse was to minimize $B_1$ inhomogeneities; nevertheless, the composite SR pulse train (product sequence used in Cartesian scans) has been shown to perform almost as well in the LV region for Cartesian imaging at 3T.

The radial pulse sequence included gradient-delay correction prospectively optimized for the scanner (see Peters D C et al. Centering the projection reconstruction trajectory: Reducing gradient delay errors. Magn Reson Med 2003; 50:1-6; which is incorporated herein by reference in its entirety), and acquisition of the radial spokes was eight-fold interleaved to minimize "smearing" artifacts caused by T1 relaxation after the SR pulse (see Adluru et al. Acquisition and reconstruction of undersampled radial data for myocardial perfusion magnetic resonance imaging. J. Magn Reson Imaging 2009; 29:466-473; and Peters et al. Inversion recovery radial MRI with interleaved projection sets. Magn Reson Med 2006; 55:1150-1156; each of which are incorporated herein by reference in their entirety). The interleaving pattern was implemented by first partitioning the total number of spokes (48 or 56) into eight uniformly spaced subsets labeled from $G_1$ to $G_8$. The acquisition order for these disjoint groups (each containing seven to eight spokes) was as follows: $\{G_1, G_5, G_3, G_7, G_2, G_6, G_4, G_8\}$.

To further reduce the effects of T1 relaxation and similarly to the KWIC scheme, the central k-space data used in the reconstruction was limited to the spokes in the middle of the acquisition window (i.e., $\{G_7, G_2\}$). Specifically, 15 central k-space samples (the DC sample and seven samples on each of its two sides) for spokes in $\{G_3, G_6\}$ and 27 central k-space samples for $\{G_1, G_5, G_6, G_4, G_8\}$ were excluded in the reconstruction (the DCF was adjusted accordingly). In addition, the radial readout direction (polarity) was alternated within each shot to reduce potential off-resonance effects (see Block K T, Frahm J. Radial single-shot STEAM MRI. Magn Reson Med 2008; 59:686-691; which is incorporated herein by reference in its entirety). Coil sensitivity profiles were computed by applying an eigenvector-based estimation method (see Walsh et al. Adaptive reconstruction of phased array MR imagery. Magn Reson Med 2000; 43:682-690, which is incorporated herein by reference in its entirety).

Image Reconstruction and Analysis

Image reconstruction for radial acquisitions was done on a frame-by-frame basis (no temporal acceleration) using non-Cartesian SENSE (sensitivity encoding) and performed offline on a workstation computer (Pentium Dual-Xeon 3.3 GHz) in MATLAB (Math-works, Natick, Mass.) employing 12 computing cores (reconstruction time: 75 s/slice). The reconstruction algorithm was according to a conjugate-gradient scheme used to implement non-Cartesian SENSE with no explicit regularization (see Pruessmann et al. Advances in sensitivity encoding with arbitrary k-space trajectories. Magn Reson Med 2001; 46:638-651; which is incorporated herein by reference in its entirety) and employing the Gaussian apodizer (Eq. [3] of this section). The kernel parameter $\Omega$ for the apodizer was chosen on the basis of the desired in-plane reconstructed resolution, which was set at 2.15×2.15 mm$^2$. Given that the acquisition resolution was 1.8 mm (isotropic in-plane), it was determined that the apodization should correspond to a 1.2-fold reduction in resolution along each dimension (1.2-fold increase in FWHM of the PSF). The inventors then used the computational framework described above (FIG. 14) and selected $\Omega$=1:24 to yield the desired apodizer. Compared with the apodized radial PSF discussed above, the peak negative PSF side lobe amplitude for this setup is −1.6% and therefore is expected to have negligible ringing components, similarly to FIGS. 14d1 and 14d2. In another embodiment, other parallel-imaging schemes that are suitable for radial acquisition can be used, such as variants of the GRAPPA method (see Griswold et al. Generalized autocalibrating partially parallel acquisitions (GRAPPA). Magn Reson Med. 2002 June; 47(6):1202-10); which is incorporated by reference herein in its entirety). Further, the image reconstruction scheme may be incorporated within the MRI scanner software thereby eliminating the need of a workstation computer and specialized software for generating and/or displaying the reconstructed images.

One representative midventricular image from each radial/Cartesian FPP image series (a total of 24 images for the 12 subjects) was selected from the "early myocardial enhancement" phase (defined as 8 R-R cycles after initial LV cavity enhancement). All representative images were visually scored for artifact by two expert readers blinded to the study protocol using a consensus scoring scheme of 0-4 (0: no artifact; 1: negligible; 2: mild; 3: moderate; and 4: severe artifact). For the radial images, the reconstructed frame (among the two to three frames per R-R cycle) that best matched the Cartesian midventricular image in terms of cardiac phase was chosen for the blind read (to "equalize" the motion effects in the visual comparison as much as possible). The following procedure was used for quantitative scoring of the artifact. Radial reconstructions were converted to DICOM images (using the scanner-produced tags) and imported in an expert viewer (Osirix; Pixmeo, Geneva, Switzerland). For quantitative evaluation, the spatial width of the DRA in each representative image was measured as a surrogate measure for its severity (see Plein et al. Dynamic contrast-enhanced myocardial perfusion MRI accelerated with k-t SENSE. Magn Reson Med 2007; 58:777-785; which is incorporated herein by reference in its entirety). In particular, spatial widths of the DRAs were computed from the interpolated DICOMs as a measure of the maximal length (largest transmural extent) of the signal dips along all polar directions (along rays starting from the cavity center and extending toward the endocardium). All statistical tests comparing radial and Cartesian results used the Mann-Whitney U test (equivalent to Wilcoxon rank-sum test) computed in MATLAB.

Results
Numerical Simulation

Figure 15:
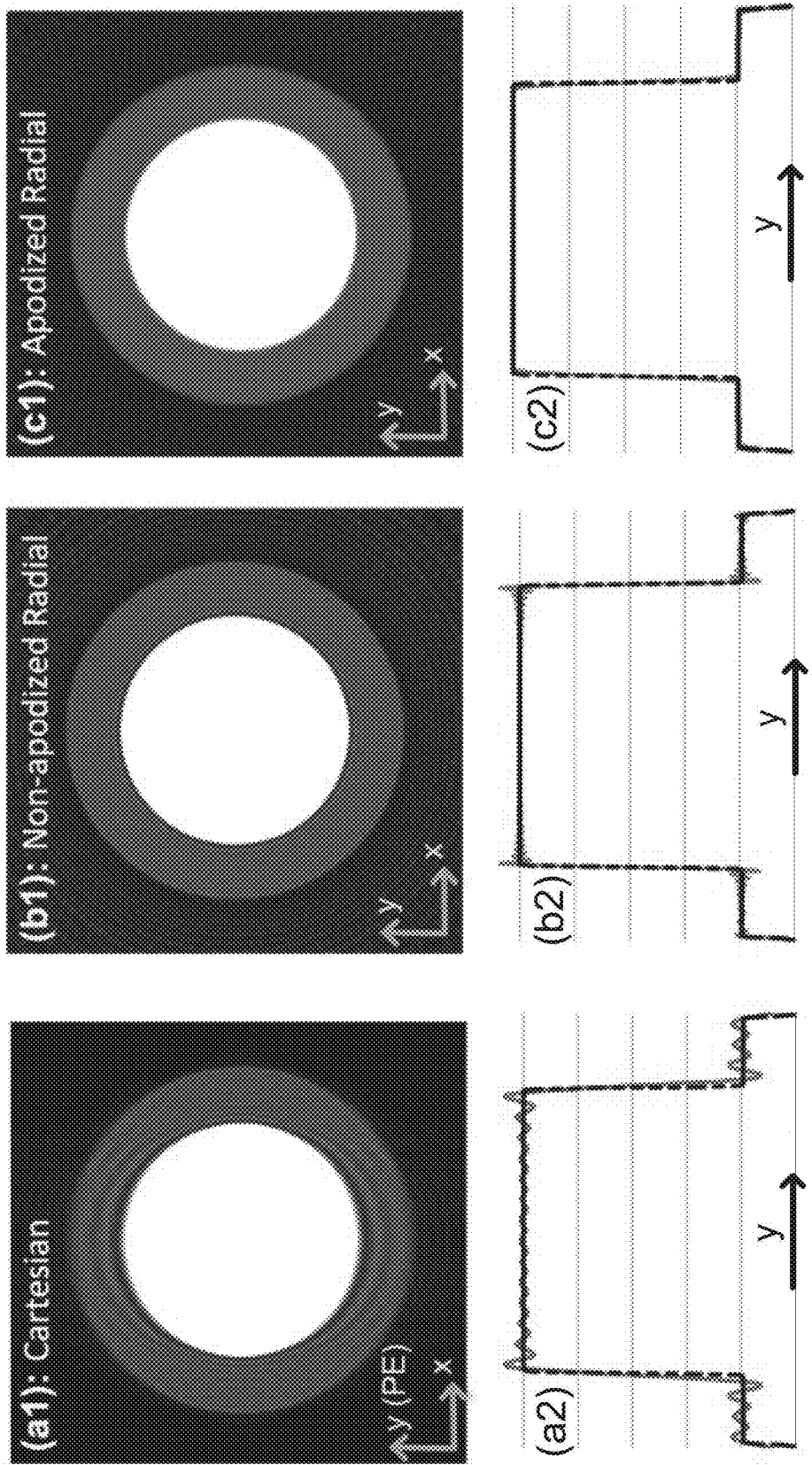
FIG. 15 depicts, in accordance with an embodiment of the invention, numerical phantom results. a1: Cartesian reconstruction of analytical disk phantom with same acquisition scheme as in FIG. 14 (three-fold lower resolution along y). b1: nonapodized radial reconstruction (same number of readouts and readout resolution). c1: Apodized radial reconstruction with the same k-space data as in panel b1 (same apodizer as for FIG. 14d). All images use zero-filled interpolation to a 512×512 image matrix. a2, b2, and c2: 1D cuts of the images in the top panel along the center of the image parallel to the y axis that are overlaid on the ground truth (dotted line). The Cartesian image in panel a1 exhibits significant ringing artifacts (Gibbs) along y (PE), whereas apodized radial reconstruction in panel c1 eliminates all ringing-induced artifacts and has reduced streaking compared with panel b1. Specifically, the energy (2-norm) of the streak region outside of the disks as a percentage of the energy of the disk phantom is 40% lower in panel c1 compared with panel b1 (11.5% versus 19%). Overall, the results verify the PSF effects described in FIGS. 13 and 14, and demonstrate that radial sampling with wide k-space coverage and apodized reconstruction can effectively eliminate the DRAs caused by Gibbs-like ringing effects.

FIG. 15 presents the simulation results for the disk-shaped numerical phantom. The top row (FIGS. 15a1-15c1) shows the reconstructed images corresponding to the PSFs in FIGS. 14b1, 14c1, and 14d1, respectively. The lower panels (FIGS. 15a2-15c2) show a 1D cut along y, which is overlaid on top of the ground truth (dotted line). As seen from the figure, the nonapodized radial reconstruction yields negligible (very thin) ringing, and the Gaussian-apodized reconstruction completely eliminates any ringing artifact, although at the cost of lower resolution. Specifically, the width of the DRA caused by Gibbs ringing in FIG. 15a1 is approximately 17% of the width of the outer disc. In contrast, this measure is 5% for the nonapodized radial reconstruction in FIG. 15b1, and is zero for the apodized reconstruction (with $\Omega=1:17$) in FIG. 15c1. Moreover, the apodized reconstruction has less streaking. Further details are provided in the figure description provided herein. In summary, the simulation results verify the PSF effects described above (FIGS. 13 and 14).

Phantom Experiment

Figure 17:
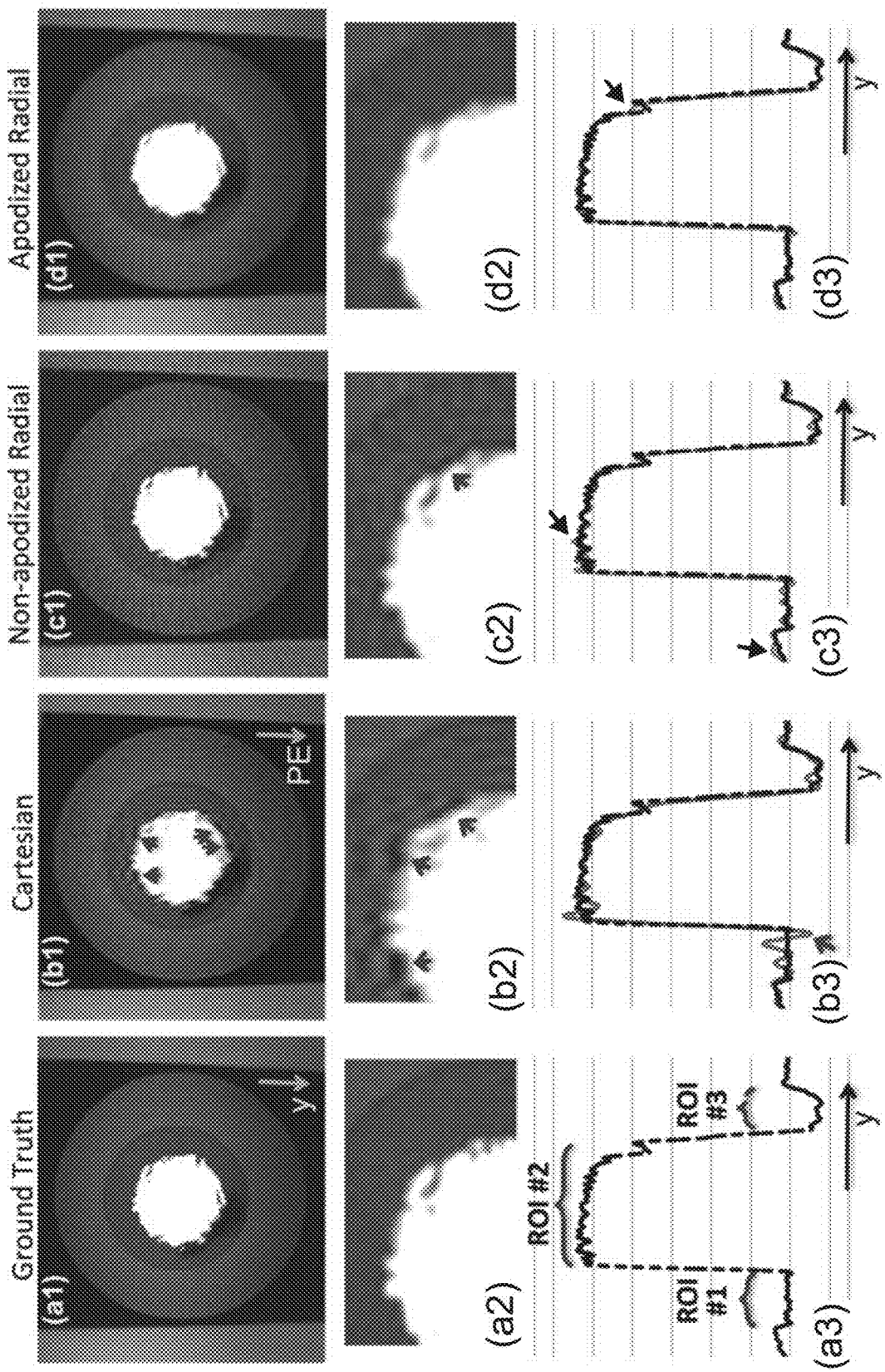
FIG. 17 depicts, in accordance with an embodiment of the invention, reconstruction results for the MR phantom in FIG. 16. The top row (a1-d1) shows zoomed-in reconstruction result: the middle row (a2-d2) shows in the top row further zoomed-in to the box in FIG. 16, and the bottom row (a3-d3) shows 1D cuts along the cut line in FIG. 16, with panel a3 overlaid on panels b3-d3 for comparison (ROIs in panel a3 are defined in FIG. 16). a1-a3: Ground truth image with 1.0×1.0 mm$^2$ resolution. All other panels correspond to reconstructions with 77 readouts (256 samples each). B1-b3: Cartesian reconstruction with 1.5×3.0=4.5 mm$^2$ resolution (FOV size=384×230 mm$^2$); the arrows in panels b2 and b3 indicate DRAs. c1-c3: Nonapodized radial reconstruction with 1.5×1.5=2.25 mm$^2$ resolution; the arrow in panel c2 points to a negligible DRA, and the arrows in panel c3 show mild streaking d1-d3: Apodized radial reconstruction (same apodizer as FIGS. 14d and 15c) with 1.92×1.92=3.7 mm$^2$ resolution (no DRAs, negligible streaking); the arrow in panel d3 points to over-smoothening of a small feature, which is a consequence of the lower resolution compared with the ground truth in panel a3.

The reconstruction results for the MR phantom are shown in FIG. 17. The first column (FIGS. 17a1-17a3) shows the ground truth image (from FIG. 16) with $1.0 \times 1.0$ mm$^2$ resolution. All other panels correspond to reconstructions of $N_{RO}=77$ readouts with Ns=256 samples per readout. The top row (FIGS. 17a1-17d1) shows cropped reconstruction results for each acquisition/reconstruction method. Zoomed-in versions of the images (highlighted box in FIG. 16) are shown in the middle row (FIGS. 17a2-17d2). The bottom row (FIGS. 17a3-17d3) shows 1D cuts of the images in the top row. The second column (FIGS. 17b1-17b3) shows the Cartesian reconstruction with $1.5 \times 3.0=4.5$ mm$^2$ resolution; arrows in FIGS. 17b2 and 17b3 point to DRAs. The third column (FIGS. 17c1-17c3) shows the nonapodized radial reconstruction with $1.5 \times 1.5=2.25$ mm$^2$ resolution. The arrow in FIG. 17c2 points to negligible (very thin) DRA, and those in FIG. 17c3 show mild streaking artifacts. Finally, the fourth column (FIGS. 17d1-17d3) shows the apodized radial reconstruction (apodizer as in Eq. [3] of this section using $\Omega=1:17$) with $1.92 \times 1.92=3.7$ mm$^2$ resolution. This is somewhat better than the overall Cartesian resolution (4.5 mm$^2$). More importantly, FIG. 17d1 exhibits no discernable DRAs and has negligible streaking. The arrow in FIG. 17d3 points to a small feature, which is somewhat over-smoothened compared with the ground truth in FIGS. 17a1-5a3 because of the lower resolution. Note that a similar resolution limitation is seen in the Cartesian image (FIG. 17b3) for reconstruction of the same feature. To quantitatively evaluate the image quality differences in FIG. 17, the inventors computed the relative contrast difference between the normal ROI (#1 in FIG. 16) and deficit ROI (#3 in FIG. 16) as a percentage of the normal ROI. This relative contrast for the ground truth image (FIG. 17a1), Cartesian image (FIG. 17b1), nonapodized radial image (FIG. 17c1), and apodized radial image (FIG. 17d1) are 79.3%, 68.1%, 70.3%, and 74.5%, respectively.

In Vivo Studies

Figure 18:
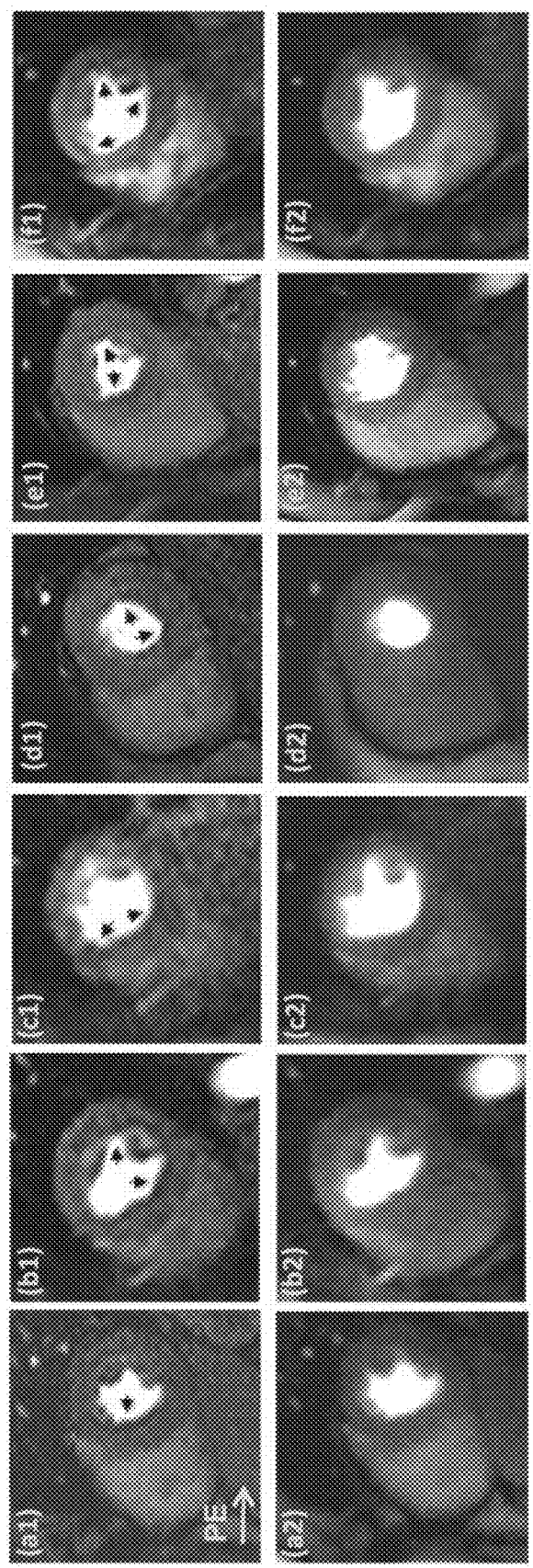
FIG. 18 depicts, in accordance with an embodiment of the invention, representative first-pass myocardial perfusion images (midventricular slice) from each of the 12 healthy volunteer studies; all images correspond to a similarly selected early myocardial enhancement phase (defined as eight R-R cycles after initial LV cavity enhancement). The first row in each panel (a1-f1 and g1-l1), shows Cartesian images (PE direction from left to right). The second row in each panel (a2-f2 and g2-l2) shows the corresponding images for the optimized radial imaging scheme. For the radial images, the reconstructed frame (among two to three midventricular frames in one R-R cycle that best matched the midventricular Cartesian image in terms of cardiac phase is shown. Arrows point to the observed DRAs. No noticeable DRA is seen in the radial images (although panel e2 shows mild streaking in the septum). Examples of qualitative artifact scores are as follows: panels a1 and a2, Cartesian=3.5 radial=0; panels i1 and i2, Cartesian=3, radial=1. The SNR in the myocardium (mean intensity divided by standard deviation in a homogenous region at peak enhancement) is similar between Cartesian and radial images (Cartesian, 10.4±2.5 versus radial, 11.7±2.2; P=0.40).
Figure 18:
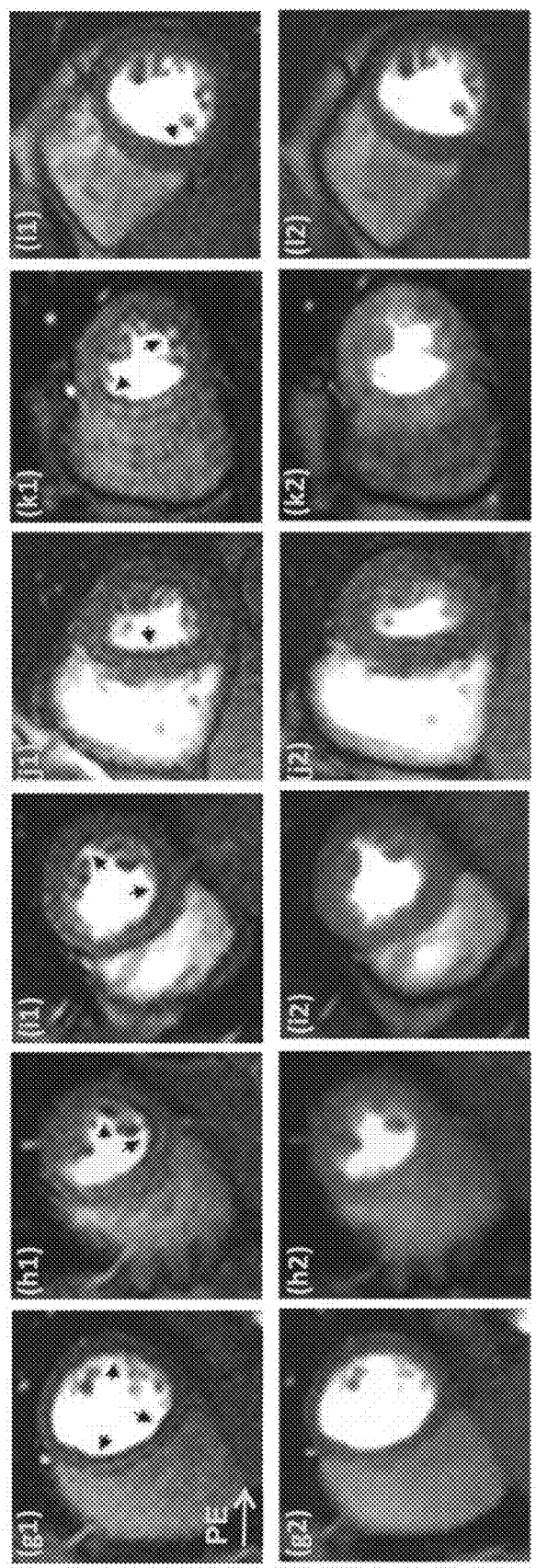
Figure 19:
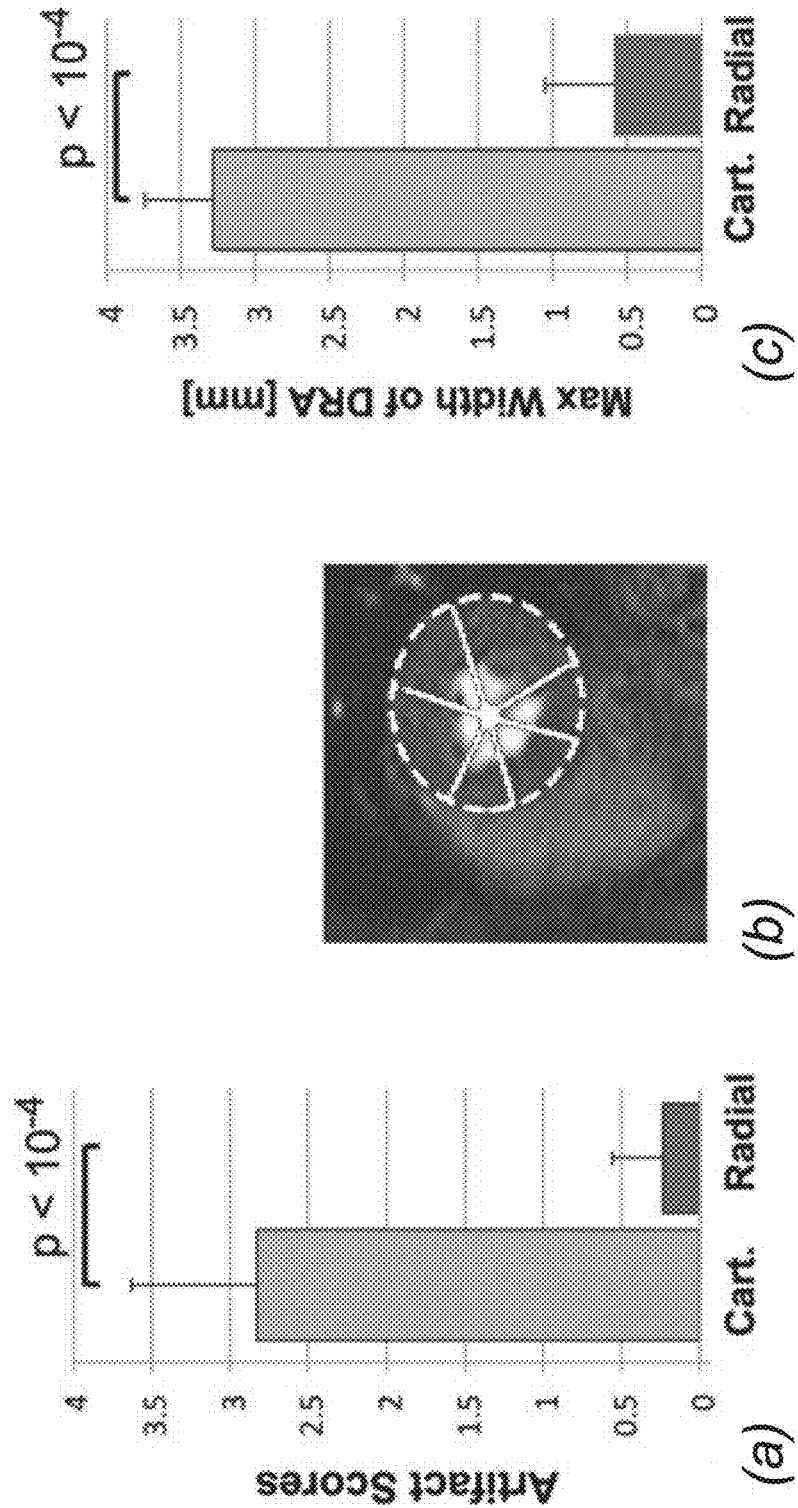
FIG. 19 depicts, in accordance with an embodiment of the invention, a: summary of artifact scores for the representative first-pass perfusion images (FIG. 18) assigned by two expert readers (consensus 0-4 scale scoring: 0, no artifact; 1, negligible; 2, mild; 3, moderate; 4, severe artifact). The results clearly show the superiority of optimized radial imaging in reducing the DRA (Cartesian, 2.83±0.8 versus optimized radial, 0.24±0.32; P<0.0001). b: Quantification scheme for measuring the maximum width (largest transmural extent) of the DRA along angular directions (as explained in the Methods section). c: Summary of the DRA width measurements as shown in panel b, indicating that the maximal width of DRA is significantly reduced with optimized radial imaging (Cartesian, 3.28±0.46 versus optimized radial, 0.58±0.47; P<0.0001). Note that quantitative DRA measurements become less accurate for subpixel widths.

Representative images from all volunteer studies (n=12) are shown in FIG. 18. The image quality in terms of the measured myocardial SNR for the radial and Cartesian images is similar (Cartesian: 10.4±2.5 versus radial: 11.7±2.2; P=0.40); however, unlike the Cartesian images, the reconstructed radial images (optimized scheme) are free of noticeable DRAs. Examples of scores and further details are provided in the figure description. FIGS. 18a1-18a2 and FIGS. 18e1-18e2 correspond to large heavyset subjects (>110 kg). FIG. 18e2 shows mild streaking (the only radial FPP image with noticeable streaking in the heart region among the 12 studies), but FIG. 18a2 does not. FIG. 19a shows mean artifact scores assigned by expert readers, clearly indicating superiority of the optimized radial imaging method in reducing the DRA (P<0.0001). 19b depicts the quantification scheme for estimating the DRA width and FIG. 19c summarizes the measurements, indicating that the DRA width is significantly reduced for optimized radial imaging (P<0.0001). In summary, the in vivo results show a very significant reduction of the DRA using the optimized radial imaging scheme, both in terms of qualitative scores and quantitative assessment.

Discussion

As demonstrated herein, the inventors developed a radial sampling strategy that, based on optimization of the associated pointspread function, eliminates ringing-induced artifacts and hence enables reconstructing first-pass myocardial perfusion images free of the DRA. For imaging experiments, the inventors developed and applied an optimized FPP imaging technique based on the proposed radial sampling scheme with wide k-space coverage, and a rather simple frame-by-frame reconstruction method (i.e., each frame is reconstructed independent of others and without temporal acceleration) using numerically optimized apodization. The inventors demonstrated the capability of the proposed method through a systematic theoretical description combined with numerical simulations in addition to phantom and in vivo experiments, as summarized in the following: First, the study described in this section highlighted the fact that, unlike conventional Cartesian sampling, radial sampling has the following property: the frequency of PSF oscillations along both spatial dimensions becomes narrower using a wider k-space readout (i.e., a higher readout resolution or $k_r^{max}$, equivalent to more samples per readout for a fixed FOV) which implies narrower (i.e., less significant) ringing artifacts for the reconstruction. Second, it was noted that widening the k-space readout yields negligible temporal resolution penalty (although it results in an expected SNR cost). Third, the inventors showed that, with a simple scheme for optimized apodized reconstruction, one can trade off in plane resolution to simultaneously eliminate the PSF oscillations—hence the associated ringing artifacts—and improve the image quality (thanks to reduced streaking and higher SNR). Fourth, and most importantly, using the proposed radial acquisition scheme with typical FPP sequence parameters, the level of apodization needed for achieving the desired PSF behavior (i.e., highly suppressed ringing/oscillatory components) is quite mild and, therefore, implies a benign loss in reconstructed resolution. The inventors specifically chose the apodization parameter (Gaussian kernel in Eq. [3] of this section) such that the effective in-plane resolution of radial images matches or slightly outperforms the typical resolution in conventional Cartesian imaging. For the presented in vivo results (FIG. 18), the radial dataset was acquired at 1.8×1.8 mm² resolution and all acquired samples were used in the reconstruction but, by applying the apodizer (Eq. [3] of this section), the inventors reconstructed the images at a lower resolution, namely, 2.15×2.15 mm², with almost no ringing-induced DRAs. The optimized apodization effectively eliminated the oscillatory side lobes in the PSF, thereby eliminating nearly all of the ringing effects. Specifically, the peak PSF side-lobe amplitude was suppressed from −13.2% for nonapodized PSF to −1.6% (i.e., an 8.3-fold reduction).

Results from in vivo studies clearly showed that the optimized radial imaging scheme can yield significant reductions in DRAs during the early myocardial enhancement phase of a FPP image series, where clinical interpretation of the DRA is most difficult. The quantitative artifact measurements (FIG. 19) show that the DRA width is on average slightly larger than 1 pixel along the PE line for Cartesian images. This is consistent with previous reports asserting that the DRA width for Cartesian imaging is typically one to two times the pixel width along the PE line. In contrast, the DRA width measurements for the optimized radial images indicate that, on average, the estimated width of the signal loss was smaller than a third of a pixel width, which is negligible. The average in-plane resolution for Cartesian images was approximately 1.8×2.8≈5.0 mm² and for radial images was 2.15×2.15≈4.6 mm², which is slightly better than the parallel imaging—accelerated Cartesian scheme. It is clear that either method will not be capable of accurately resolving myocardial features that are smaller than 5 mm² in area (roughly 2 mm along x and y for radial images). Nevertheless, the 2.15×2.15 mm² resolution achieved by the radial FPP method is considered relatively high among conventional FPP schemes that do not use advanced reconstruction methods and/or temporal acceleration. For all in vivo studies, the inventors deliberately performed the radial scans as the first perfusion scan (before Cartesian), which may have disadvantaged the radial FPP scans in terms of the effect of residual contrast in potentially reducing DRAs for subsequent FPP scans.

In addition to ringing effects, there may be other potential contributing factors to the DRA as listed above. Furthermore, it is difficult to decouple the contribution of each factor (e.g., motion versus ringing). Nevertheless, the left-to-right pattern of the observed DRAs in Cartesian images matches the PE direction (FIG. 18) and is consistent with described PSF ringing effects (FIGS. 14b1, 15a1, and 17b1). Furthermore, the relatively low heart rates (rest scan), relatively small acquisition window (≈135 ms) and contrast dose (0.04 mmol/kg), all combined with short echo times (1.3-1.4 ms), alternating readout-direction radial acquisition, and local cardiac shimming should minimize the motion and susceptibility effects. All of these observations—in conjunction with the obtained results and derivations—indicate that the main driver for reducing DRAs in the in vivo studies described herein is elimination of the PSF ringing effects, achieved by using the optimized radial imaging scheme. It is worth mentioning that a similar apodization scheme (tapered weighting of k-space data) can also be applied to the other non-Cartesian (see Salerno et al. Myocardial perfusion imaging with variable density spiral trajectories. In proceedings of the 18th Annual Meeting of ISMRM, 2010. P. 3624; which is incorporated herein by reference in its entirety) or even Cartesian (see Di Bella et al. On the dark rim artifact in dynamic contrast-enhanced MRI myocardial perfusion studies. Magn Reson Med 2005; 54:1295-1299; which is incorporated by reference herein in its entirety) datasets to reduce the ringing effects; however, for Cartesian data sets, the apodization will reduce the already-low PE resolution to unacceptable levels.

Relation to Previous Work

Recent studies using high-resolution Cartesian imaging with temporally accelerated k-t schemes have shown success in reducing DRAs by decreasing the spatial width of Gibbs ringing effects as compared with conventional Cartesian schemes. These results imply that Gibbs ringing is most likely a significant, if not the dominant, contributing factor to the DRA. However, achieving such resolutions (1.3-1.8 mm isotropic in-plane) with Cartesian imaging inevitably requires a high level of temporal acceleration, which has its own issues: the possibility of reduced temporal fidelity or loss of robustness due to modeling ("training data") assumptions especially with regard to breathing motion, and a need for specialized computational platforms. Furthermore, taking this approach, there is always the possibility that the images would still exhibit ringing-induced DRAs with a 1- to 2-pixel width (e.g., the mean DRA width for rest imaging was reported to be 1.3-2.7 mm by Maredia et al. (see Maredia et al. Effect of improving spatial or temporal resolution on image quality and quantitative perfusion assessment with k-t SENSE acceleration in first-pass CMR myocardial perfusion imaging. Magn Reson Med 2010; 64:1616-1624; which is incorporated herein by reference in its entirety). In contrast, the inventive approach described in this section is based on sampling design and optimization of the PSF without a need for additional acceleration beyond conventional parallel imaging. Indeed, the imaging experiments presented in this section were performed using frame-by-frame reconstruction (i.e., without temporal acceleration). Moreover, the inventors refrained from using highly accelerated (e.g., compressed sensing or nonlinearly regularized) reconstruction to achieve a fair comparison with the conventional Cartesian imaging scheme. However, incorporation of an edge-preserving regularized reconstruction scheme, such as 2D total variation regularization combined with non-Cartesian SENSE, would improve the image quality, and is within the scope of the present invention and enabled by the description above.

Conclusions

Based on a series of systematic investigations, from theoretical and phantom experiments to in vivo studies, it was demonstrated that optimized radial first-pass perfusion imaging with wide k-space coverage and a simple reconstruction method can effectively eliminate ringing-induced DRAs while providing equivalent resolution and similar image quality as conventional Cartesian imaging.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for performing first-pass myocardial perfusion magnetic resonance imaging (MRI) on a subject, comprising:
    using an MRI machine to apply a pulse sequence with continuous radial k-space sampling to a volume of interest (VOI) comprising a region of a heart of the subject, T1 weighting of the volume of interest being provided by a steady state magnetization of the pulse sequence resulting from the continuous radial k-space sampling, the pulse sequence having a flip angle selected so as to maximize a ratio of (i) a contrast-to-noise ratio of hypoperfused tissue to (ii) a contrast-to-noise ratio of non-perfused tissue;
    introducing a contrast agent into a vascular system of the subject's prior to or during imaging; and
    using a model-based, iterative image reconstruction technique to generate one or more perfusion images of one or more slices or VOIs within the heart region, the image reconstruction technique including utilizing a sliding window scheme to generate the one or more perfusion images, the one or more perfusion images being indicative of passage of the contrast agent through at least the region of the heart of the subject.

2. The method of claim 1, wherein no electrocardiogram (ECG) signal acquisition is required during the MRI.

3. The method of claim 1, wherein an apodization scheme is employed in the image reconstruction technique to reduce or eliminate a dark-rim artifact.

4. The method of claim 1, wherein the one or more perfusion images depict the heart or a portion thereof within 30 to 60 heartbeats after the introduction of the contrast agent.

5. The method of claim 4, wherein an apodization scheme is employed in the image reconstruction technique to reduce or eliminate a dark-rim artifact.

6. The method of claim 1, wherein the one or more perfusion images include multiple image frames generated per each heartbeat at a rate of at least 8 image frames per second to depict the heart motion.

7. The method of claim 1, wherein the Mill machine is a 3.0T scanner.

8. The method of claim 1, wherein the subject has an arrhythmia.

9. The method of claim 1, further comprising diagnosing the subject with the presence or absence of a condition associated with a perfusion defect or a wall motion abnormality, based upon the one or more images.

10. A magnetic resonance imaging system, comprising:
a magnet operable to provide a magnetic field;
a transmitter operable to transmit to a region within the magnetic field;
a receiver operable to receive a magnetic resonance signal from the region; and
a processor operable to control the transmitter and the receiver; wherein the processor is configured to direct the transmitter and receiver to execute a sequence, comprising:
applying a pulse sequence with continuous radial k-space sampling to a volume of interest (VOI) comprising a region of a heart of a subject, T1 weighting of the VOI being provided by a steady state magnetization of the pulse sequence resulting from the continuous radial k-space sampling, the pulse sequence having a flip angle selected so as to maximize a ratio of (i) a contrast-to-noise ratio of hypoperfused tissue to (ii) a contrast-to-noise ratio of non-perfused tissue;
acquiring magnetic resonance data from the VOI in the subject; and
generating one or more images based on the magnetic resonance data using a model-based, iterative image reconstruction technique that includes a sliding windows scheme, the one or more images being indicative of passage of a contrast agent through at least the region of the heart of the subject.

11. A non-transitory machine-readable medium having machine executable instructions for causing one or more processors of a magnetic resonance imaging (MRI) machine to execute a method, comprising:
applying a pulse sequence with continuous radial k-space sampling to a volume of interest (VOI) comprising a region of a heart of a subject, T1 weighting of the VOI being provided by a steady state magnetization of the pulse sequence resulting from the continuous radial k-space sampling, the pulse sequence having a flip angle selected so as to maximize a ratio of (i) a contrast-to-noise ratio of hypoperfused tissue to (ii) a contrast-to-noise ratio of non-perfused tissue;
acquiring magnetic resonance data from the VOI in the subject; and
generating one or more images based on the magnetic resonance data using a model-based, iterative image reconstruction technique that includes a sliding windows scheme, the one or more images being indicative of passage of a contrast agent through at least the region of the heart of the subject.

12. The non-transitory machine-readable medium of claim 11, wherein the NMI machine is a 3.0T machine.

* * * * *